United States Patent [19]

Frommer et al.

[11] 4,065,557

[45] Dec. 27, 1977

[54] AMINO SUGARS AND THEIR USE IN IMPROVING THE MEAT:FAT RATIO IN ANIMALS

[75] Inventors: Werner Frommer, Wuppertal; Horst Gericke, Leichlingen; Uwe Keup, Wuppertal; Walter Puls, Wuppertal; Delf Schmidt, Wuppertal; Otto Wagner, Wuppertal, all of Germany

[73] Assignee: Bayer Aktiengesellschaft, Germany

[21] Appl. No.: 704,842

[22] Filed: July 13, 1976

Related U.S. Application Data

[63] Continuation-in-part of Ser. No. 557,264, March 11, 1975, abandoned.

[30] Foreign Application Priority Data

Mar. 21, 1974 Germany .............................. 2413720

[51] Int. Cl.² .................. A61K 31/71; A61K 31/715; C12D 13/04
[52] U.S. Cl. .................................. 424/181; 195/31 P; 195/80 R; 195/31 R; 424/180; 536/1; 536/4; 536/18; 260/307 F

[58] Field of Search ................. 424/180, 181; 536/18, 536/4

[56] References Cited

U.S. PATENT DOCUMENTS 3,876,766   4/1975   Frommer et al. .................... 424/115

*Primary Examiner*—Johnnie R. Brown
*Attorney, Agent, or Firm*—Jacobs & Jacobs

[57] ABSTRACT

Glucopyranosyl and oligoglucosidyl derivatives of 4,6-bisdesoxy-4-(4,5,6-trihydroxy-3-hydroxymethylcyclohex-2-en-1-ylamino)-α-D-glucopyranose, which are inhibitors of glycoside hydrolases of the digestive tract, favorably improve the meat:fat ratio in animals in favor of a higher proportion of meat. A single amino-sugar or a mixture of amino-sugars can be formulated in combination with an edible carrier and fed to animals. A representative embodiment is a pig feedstuff in admixture with O-{4,6-bisdesoxy-4-[1S-(1,4,6/5)-4,5,6-trihydroxy-3-hydroxymethylcyclohex-2-en-1-ylamino]-α-D-glucopyranoxyl}-(1→4)-O-α-D-glucopyranosyl-(1→4)-D-glucopyranose.

38 Claims, No Drawings

AMINO SUGARS AND THEIR USE IN IMPROVING THE MEAT:FAT RATIO IN ANIMALS

CROSS-REFERENCE

This is a continuation-in-part of Ser. No. 557,264 filed Mar. 11, 1975, now abandoned.

DETAILED DESCRIPTION

The present invention relates to the use of certain amino-sugars which when orally administered to animals influence the utilization of feed by reducing formation of fat, thereby increasing the meat:fat ratio of the animal in favor of a higher proportion of meat, and to compositions adapted for such use.

In particular the invention pertains to compositions comprising at least one amino-sugar in combination with an edible carrier, the amino-sugar being one which is obtainable as a product upon the fermentation of a microorganism of the family Actinoplanaceae and chemically consisting of a 4,6-bidesoxy-4-(4,5,6-trihydroxy-3-hydroxymethlcyclohex-2-en-1-ylamino-α-D-glucopyranose of the formula:

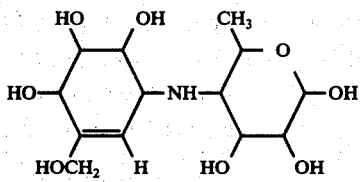

glycosidically linked with $n$ glucose residues, where $n$ has a value of from 1 to 40, the amino-sugar upon total acid hydrolysis yielding the compound

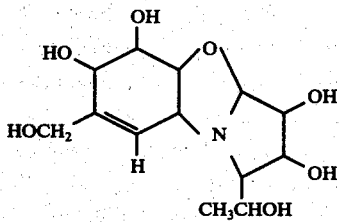

and glucose in a molar ratio of 1:$n$. When $n$ is greater than 1, the glucose units, when present in a polymeric chain of two or more glucose residues, are linked α-1:4.

It is known that a number of microorganisms of the order Actinomycetes, particularly those of the family Actinoplanaceae, produce materials which inhibit glycoside hydrolases. U.S. Pat. No. 3,876,766, for example, describes methods for producing such materials from a number of microorganisms. The materials obtained fall into two broad group: (a) oligosaccharides or polysaccharide derivatives and (b) inhibitors of a peptide nature. U.S. Pat. No. 3,855,066 describes an improvement in which materials having significantly higher levels of amylase activity are obtained from Actinoplanaceae CBS strain 614.71, preferably by culturing in the presence of 4 to 6% starch. U.S. Pat. No. 3,879,546 describes a further refinement in which polysaccharidic or oligosaccharidic materials having primarily amylase inhibiting properties can be converted to materials having a higher level of saccharase inhibiting properties through hydrolytic techniques (acidic or enzymatic hydrolysis) by which mono-, di- and trisaccharide units are cleaved fronm the inhibitor molecules. The direct preparation of materials having predominantly saccharase inhibiting properties through the use of a starch free nutrient solution, preferably in the presence of maltose, has also been described in copending application Ser. No. 481,224., filed June 20, 1974, now U.S. Pat. No. 3,937,817.

Copending application Ser. No. 654,627, filed Feb. 2, 1976 as a continuation-in-part of Ser. No. 506,550 filed Sept. 16, 1974 now abandoned, describes certain new amino-sugars which are individually obtained in molecularly homogeneous form and which, in their pure state, exhibit highly advantageous and unexpected properties in the therapeutic treatment of diabetes, adiposity and hyperlipemia.

The present invention is based on the discovery that these amino-sugars when administered orally to animals improve the meat:fat ratio in favor of a higher proportion of meat. The reduced formation of fat thus increases the leaness of the meat.

In production of processed animal products including livestock raising, it is, of course, of great economic importance to produce animal carcasses having the lowest possible proportion of fat and the highest possible proportion of lean meat, and thus a high proportion of protein, without producing an adverse influence on the animal carcass. The favorable influence on the ratio of the amount of undesired fat to the amount of desired low-fat meat (lean meat) in favor of the lean meat is of particular importance in raising and maintaining of fatstock, for example pigs, and also in raising and maintaining other livestock and pets. The use of the present amino-sugars moreover leads to a considerable rationalizatin in feeding the animals. Since the amino-sugars cause some delay in digestion, the residence time of the nutrients in the digestive treat is lengthened, which in many cases permits ad libitum feeding associated with little expense. Futhermore, the use of the compounds in many cases results in a considerable saving of valuable protein in feedstuffs.

The compositions of the present invention are also useful in generally avoiding undesired adiposity in animals. In addition, the compositions can be used to reduce undesired adiposity in domestic animals, such as dogs.

The compositions may contain a single amino-sugar or a mixture of amino-sugars. In either case, the amino-sugar can be in crude form or in a pure form. If the crude form does not contain any by-products having adverse effects on the desired result, there is a further advantage in that the amino-sugars need not be subjected to a costly purification process before utilization.

When the amino-sugars are combined with a feedstuff, water or other edible carrier, it is preferable that they are present in a final consumable amount of 0.001 to 5.0% by weight, and especially 0.02 to 2.0% by weight, of the material consumed. The amino-sugars can be combined with premixes containing from 0.1 to 50%, especially 0.5 to 5.0%, by weight of the amino-sugar in addition to any desired edible excipients and/or mineral salts, such as carbonated feedstuff, lime and the like. Mixed feedstuffs preferably contain 0.001 to 5.0%, especially 0.02 to 2.0% by weight of the amino-sugar together with the customary components of a mixed feedstuff, such as for example shredded cereals or cereal by-products, shredded oilcakes, animal protein, minerals, trace elements and vitamins.

The amino-sugar can also be formulated into conventional veterinary compositions for individual oral administration to animals.

If desired, the compositions of the present invention can be fed to the animals before or after the animal's regular consumption of food or drinking water.

The compositions which are particularly useful however are those which provide the amino-sugar in combination with the animal's regular drinking water or regular food, thus permitting the animal to take the amino-sugar derivatives during the normal feeding cycle. The compositions may include other active compounds such as mineral salts, trace elements, vitamins, proteins, energy sources such as starch, sugar and fats, although obviously fats should be kept low.

The amino-sugars thus can be combined with any customary commercially available or generally utilizable feedstuff composition which is suitable to be fed to animals and which may include proteins, vitamins, and minerals which are required for balanced nutrition. The feedstuff can be composed of vegetable substances such as shredded oilcakes, shredded cereals and cereal by-products, or of hay, silage, beet and other forage plants, of animal matter, for example meat products and fish products, bonemeal, fats, vitamins such as vitamins A, D, E, K and B complex, as well as special sources of protein, such as yeasts and certain amino acids and mineral substances and trace elements, such as phosphorus, iron, zinc, manganese, copper, cobalt, iodine and the like. If desired, the amino-sugars can be protected against light, air and moisture by suitable agents such as nontoxic waxes or gelatins with which they are coated before being added to the feedstuff or premix.

While the amount of amino-sugar derivative to be administered to a particular animal can be varied within wide limits, it is preferable if approximately 0.5 mg/kg to 2.5 g/kg, especially from about 10 mg/kg to about 100 mg/kg, of body weight are consumed per day. The period of administration can range from a few hours or days up to several years depending on the circumstances and the particular animal. The suitable amount of active amino-sugar derivative and the duration of administration are directly related to the feeding objective.

The effectiveness of the compositions of the present invention is dependent to some degree on the species and gender of the particular animals, Thus, the compositions of the present invention are particularly valuable in the case of animals which have a tendency for a larger amount of fat, such as warm-blooded animals including conventional livestock such as cattle, pigs, horses, sheep and goats, rabbits and other animals raised for fur such as mink and chinchilla, domestic animals such as dogs, cats, guinea pigs and hamsters, laboratory and zoo animals such as rats, mice and monkeys, poultry such as chickens, geese, ducks, turkeys, pigeons, parrots and canaries, and cold-blooded animals such as fish, for example carp, and reptiles, such as snakes can also be treated.

The compounds utilized in the present method and compositions are all amino-sugars. These can be obtained by culturing a microorganism of the family Actinoplanaceae. The compounds can also be obtained enzymatically and chemically, and the microorganism source is significant for purposes of characterization.

These amino sugars include a first group falling within the formula:

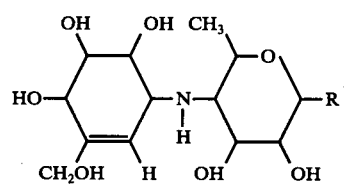

wherein R is a monosaccharide or an oligosaccharide chain of up to 40 monosaccharide units, in particular glucose or oligosaccharides of glucose. From a practical standpoint, those compounds having from 1 to 8 glucose units, and in particular 1, 2, 3 or 4 glucose units, are most satisfactory for purposes of the present invention.

It has also been found that the microbiological method of preparation results in the production of isomeric forms of these amino-sugars having three or more glucose units, in particular compounds in which one or more, but not all, of the glucose units are bound through the 4-position of the depicted cyclohexene ring.

Each of these isomeric forms; i.e. those of Formula I wherein R is an oligosaccharide unit of several glucose units and those wherein one or more of these glucose units are bound to the 4-position of the cyclohexane ring can be utilized in the present invention. Both groups can thus be depicted by the formula:

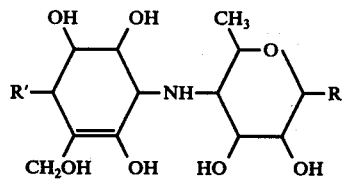

where R' is hydroxy or one to seven glucose residues, and R is one to eight glucose residues, the total of glucose residues embraced by R' and R being from 1 to 8.

Generally, but not always, the group R will embrace 1, 2 or 3 glucose residues and when R' is other than hydroxy, R will embrace two glucose residues. These residues are glycosidically linked α-1:4.

A preferred group of amino sugars for the present method and compositions are those of the conformational structure:

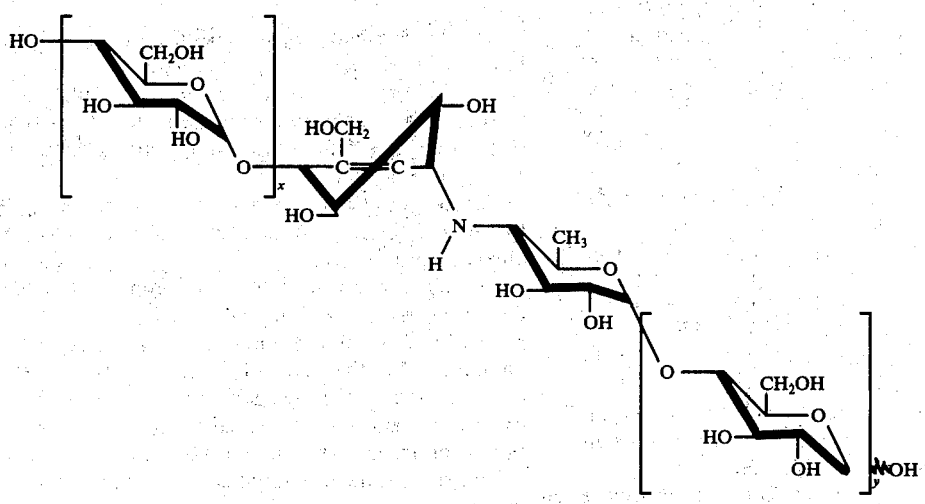

IIA wherein
y has a value of 1 to 8 and
x has a value of from 0 to 7,
the sum of y + x being from 1 to 8.

Within this preferred group, the compositions and method will most preferably be a mixture of amino-sugars in which the average value for the sum of y + x is from 1 to about 4, especially 1 to about 3, or a single substantially pure amino-sugar for which the sum of y + x is 1, 2, 3 or 4, particularly 1, 2 or 3.

The microbiological preparation of these various compounds, their purification and their chemical characterization is more fully described in copending application Ser. No. 654,627. Briefly, a microorganism of the family Actinoplanaceae and of the order Actinomycetales, preferably a strain of the genus Actinoplanes, such as Actinoplanes spec. SE 50 (CBS 961.70), SB 18 (CBS 957.70) and SE 82 (CBS 615.71), or mutants or variants thereof, is cultured in a now known manner. Strains SE 50/13 (CBS 614.71) and SE 50/110 (CBS 674.73) have proved to be particularly suitable with regard to the total yield. The description of both strains corresponds largely to that of the parent strain SE 50 (CBS 971.60) from which these strains have been obtained by natural selection without using mutagens. A solid or liquid, especially liquid, aqueous nutrient media is used, with the addition of the usual sources of carbon, sources of nitrogen salts and antifoaming agents in customary concentrations. The carbon sources used are generally carbohydrates, especially starch, maltose, glucose and mixtures of two or three of these material complex mixtures, such as commercially available malt extract. The nitrogen sources include the customary complex mixtures, such as casein hydrolysate, yeast extract, peptone, fishmeal, fish solubles, corn steep liquor, meat extract and mixtures thereof, as well as amino acids and/or ammonium salts. The culture is carried out aerobically in aerated shaken flasks or in conventional culture containers.

As is known, the nature and concentration of the source of carbon, in combination with the particular strain used for the fermentation, influences the nature of the product. In nutrient solutions which contain more than 2 wt. % of starch, compounds containing a total of 4 to 7 hexose units are predominantly formed and use of the strain SE 50/13 (CBS 614.71) in particular favors this type of production. Under certain circumstances, as little as 0.1 to 3 wt. % of starch in a nutrient solution which also contains adequate glucose (about 3.5 wt. %) will produce mixtures of several amino sugars having 4 to 7 hexose units. Such conditions yield the higher compounds which are suitable as starting materials for the lower members upon subsequent hydrolytic treatment.

On the other hand, use of starch-free nutrients, especially with the addition of maltose when using strain SE 50 (CBS 961.70), produces mixtures of compounds in which di- and trisaccharides predominate. Nutrient solutions which contain only glucose as the source of carbon have proved particularly suitable for preparation of material in which the compound in which R is one glucose residue predominates.

None of these conditions however produces a single compound to the exclusion of the other. If the nutrient solution contains excess glucose, the longer-chain compounds are also formed if the duration of fermentation is prolonged. This can be avoided, with certain limits, if exhaustion of the nitrogen sources coincides during fermentation with the exhaustion of glucose. On the other hand, if the glucose is dispensed with entirely in the nutrient solutions and maltose is added as the source of carbon, material in which the compound has two hexose units is obtained predominantly. The pure maltose can be replaced by cheaper material such as, for example, "Maltzin", a natural malt extract, and depending upon the content of maltotriose, the next-higher oligosaccharide material is also formed. The strain SE 50/110 (CBS 674.73) has proved to be particularly suitable for the preparation of material rich in the lower chain compounds containing 1, 2 or 3 glucose units. In optimal nutrient solutions, this strain produces a yield of lower chain material about twice that produced by SE 50/13 (CBS 614.71). Incubation temperatures generally lie between 15° and 45° C, preferably between 24° and 32° C. However longer chain material containing 4 to 7 glucose units are produced with SE 50 (CBS 961.70) and SE 50/13 (CBS 614.71) at a higher temperature, for example, 28° C. Shorter chain material containing 1, 2 or 3 glucose units are obtained using strains SE 50 (CBS 961.70) and SE 50//110 (CBS 674.73) at a lower temperature, for example, 24° C. The duration of culture is generally 1 to 8 days, preferably 2 to 6 days and here again longer durations of culture, especially if an excess of carbohydrate is used, favor the formation of the longer chain material.

The pH of the culture medium will range from 5.0 to 8.5, generally 60 to 78. The end point of the fermentation can be determined by determining the inhibitory activity content in an enzymatic inhibition test and by determining the composition by thin layer chromatography.

Material rich in the shorter chain compounds can be obtained from the longer chain material by chemical or enzymatic hydrolysis of monosaccharide units. Chemical hydrolysis is carried out in 1 to 5N aqueous mineral acid at 50° to 100° C., especially at 90° to 100° C., over a period of 10 to 180 minutes. Enzymatic hydrolysis is carried out by incubation with a suitable hydrolase, especially a β-amylase, an α-amylase that is not inhibited by the compounds of the invention, or an amyloglucosidase of microbial origin such as from *B. subtilis*. Hydrolysis can also be carried out microbially by culturing a suitable microorganism, for example, *Aspergillus niger* ATCC 11,394, in a nutrient medium containing 1 to 10% of the amino sugar as the sole carbon source.

The pure compounds are obtained from the foregoing products of either the Actinomycetes culture broths or the hydrolysis.

The isolation, and purification, of the individual compounds starts either from microbiological culture broths or from acid hydrolysates or from incubation mixtures in which the enzymatic and/or microbiological restructuring or degradation of the higher members of the amino sugar derivatives has been carried out.

The longer chain material containing 4 to 8 glucose units is initially separated, after prior decolorizing and concentration of the solutions, by direct precipitation. This material is further processed as discussed hereafter.

The shorter chain compounds containing 1 to 3 glucose units are initially isolated by adsorption on active charcoal at a neutral pH, with subsequent desorption utilizing aqueous alcohols or acetone, especially 50 to 80% strength acetone. The desorption can be carried out completely at acidic pH values in the range of pH 1.5 to 4, preferably pH 2 to 3. If the starting solutions are very dark in color, they are decolorized prior to the adsorption by means of active charcoal, utilizing acidic pH values (pH 1 to 3), or with nonspecific adsorption resins, for example, Lewapol CA 9221/0.35 mm particle size (Bayer AG) in a pH range of 2 to 7, preferably 2 to 3. The active charcoal preferentially binds colored material in the acid range only, while Lewapol does not absorb the amino sugar derivatives either at neutrality or in the acid range.

In order to separate the pure compounds, their weakly basic character can be utilized. Under suitable conditions, namely a pH 1 to 8, preferably pH 2 to 4, and at low ionic strength corresponding to a conductivity of less than 10 mS.cm$^{-1}$, preferably less than 2 mS.cm$^{-1}$, the compounds are bound by strongly acid cation exchanges, such as for example Dowex 50 W (Dow Chemicals) in the protonated form. The compounds can be bound particularly successfully from an acetone solution (50% to 80% acetone, pH 1 to 5, preferably 2 to 4) to cation exchangers, which, under these conditions, exhibit a substantially enhanced adsorptive capacity for the compounds. If the solution contains more than 50% of acetone, it is also possible to bind the compounds to weakly acid exchangers such as Amberlite IRC-50 (protonated form).

Aqueous solutions of acids or bases, preferably ammonia or hydrochloric acid, particularly in concentrations of 0.01 to 1 Eg./L, are best used for desorbing the compounds of the invention from the cation exchangers.

The desorbates are neutralized with a weak acidic or basic ion exchanger, or the base acid is stripped from the desorbates in vacuo, and the compounds are obtained, after concentration of the solution, by lyophilization or by precipitation with organic solvents such as 10 to 20 volumes of acetone.

Furthermore, it has proved possible to separate the lowmolecular compounds from inert saccharides by chromatography on exchangers based on cellulose, preferably phospho-cellulose (Serva, Heidelberg). Buffers, preferably phosphate buffers, of low ionic strength, preferably 2 to 10 mM and especially 5 to 10 mM, and having a pH in the range of 2.5 to 8, preferably at pH 5 to 6, are used as running agents. A prerequisite for effective fractionation is that the salt contents in the preparation to be fractionated should be as low as possible.

To prepare the individual compounds in a pure state, the pre-purified preparations, prepared as described above, are chromatographed using a suitable molecular sieve, such as for example, Bio-Gel P-2 (Bio-Rad, Munich). Fractions of the eluate are examined by thin layer chromatography and those which contain the pure compounds of the present invention are combined, rechromatographed and finally lyophilized after concentration, or precipitated by means of organic solvents, as described above.

The compounds used in the present invention are, chemically, carbohydrates. They form a series of which the amino sugar derivative [C$_{19}$H$_{33}$O$_{13}$N] is to be regarded as the initial member; i.e. R is a single glucose residue. The remaining compounds can be deemed to the higher members of this series, successively having one or two additional units of glucose. All members of this series are characterized in that upon total acid hydrolysis, "component I" [C$_{13}$H$_{19}$O$_7$N] and glucose are formed. "Component I" has been shown to have the structural formula:

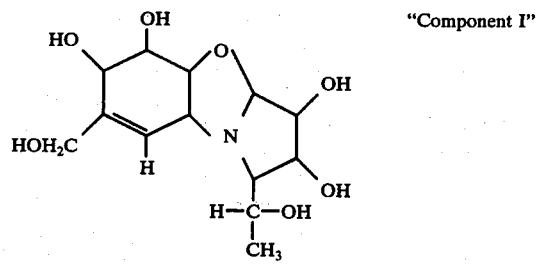

"Component I"

This compound, which has a strong anti-hyperglycemic action, is the subject of previously copending but now abandoned United States application Ser. No. 506,549, filed Sept. 16, 1974.

The initial member of the series has one glucose unit. This compound is a colorless, amorphous solid of good solubility in water, dimethylformamide, dimethylsulfoxide, methanol and hot ethanol. On thin layer chromatography using 10:6:4 (v/v) ethyl acetate:methanol:water, the compound shows an R$_f$ value of 0.46 (maltose = 0.50 and glucose = 0.65) on F 1500 silica gel films (Schleicher & Schull) and of 0.47 (maltose = 0.54 and glucose = 0.66) on F 254 silica gel plates (Merck, Darmstadt). A brown-black coloration is obtained at room temperature or after slight warming upon application of silver nitrate/sodium hydroxide spray reagent.

Spectroscopic data and chemical properties show the following structure for this compound.

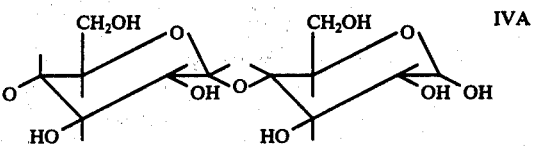

IVA 0.33 on F 254 silica gel plates using the system described above.

Chemical and spectroscopic properties show the following structure for this compound:

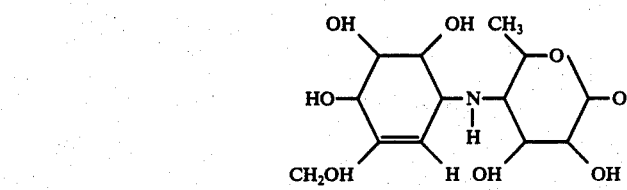

IIIA

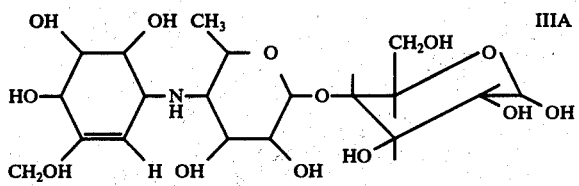

More particularly, the second member of this series is the compound O-{4,6-bisdesoxy-4-[1 S-(1,4,6/5)-4,5,6-trihydroxy-3-hydroxymethylcyclohex-2-en-1-ylamino]-α-D-glucopyranosyl}-(1→4)-O-α-D-glucopyranosyl-(1→4)-D-glucopyranose of the conformational structural formula:

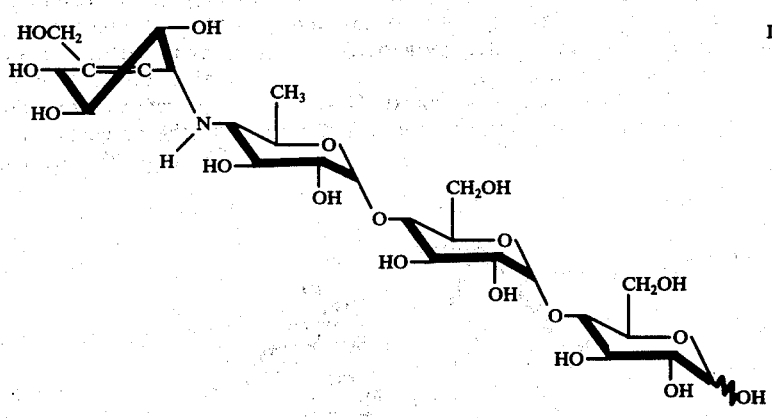

IVB

More particularly the NMR spectra demonstrates that the initial member is the compound O-{4,6-bisdesoxy-4-[1 S-(1,4,6/5)-4,5,6-trihydroxy-3-hydroxymethylcyclohex-2-en-1-ylamino]-α-D-glucopyranosyl}-(1→4)-D-glucopyranose of the conformational structural formula:

The next higher member of the series is obtained in lower than expected yields with an isomeric compound being predominantly formed. On acid partial hydrolysis, both these compounds can be split to give the first member of the series and glucose in the molar ratio of 1:2.

The material present in lower amounts is the compound O-{4,5-bisdesoxy-4-[1 S-(1,4,6/5)-4,5,6-trihydroxy-3-hydroxymethylcyclohex-2-en-1-ylamino]-α-D-glucopyranosyl}-(1→4)-O-α-D-glucopyranosyl-(1→4)-O-α-D-glucopyranosyl-(1→4)-D-glycopyranose of the conformational structural formula:

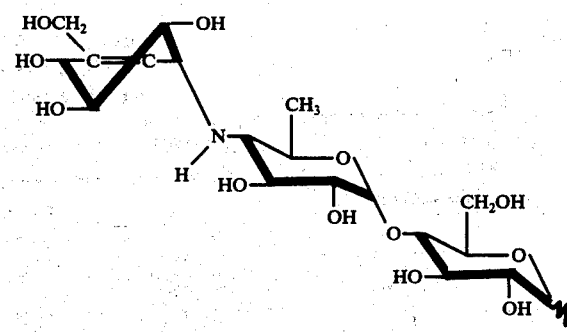

IIIB

The next member of the series has the formula $C_{25}H_{43}O_{18}N$ and is a readily water-soluble amorphous solid product. On thin layer chromatography it demonstrates an $R_f$ value of 0.35 on F 1500 silica gel films and

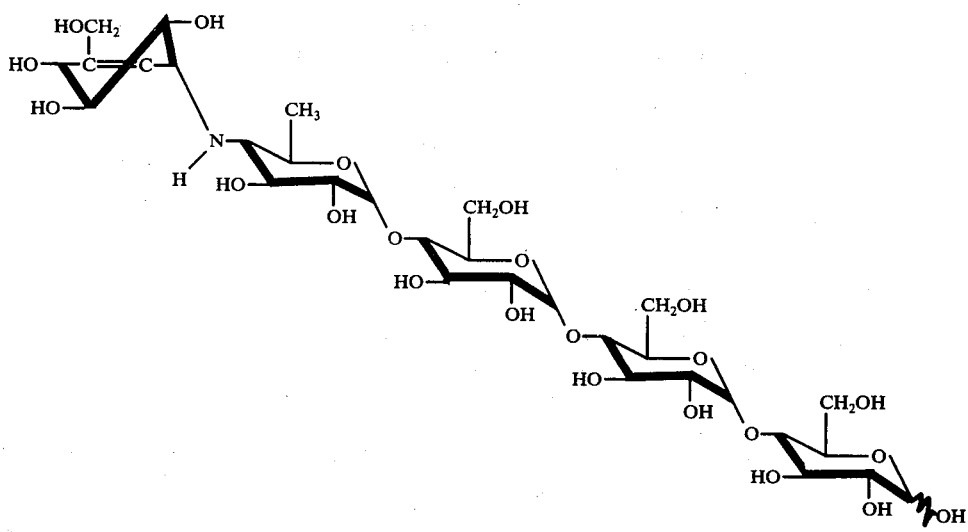

The isomeric material present in larger amounts is the compound O-{4,6-bisdesoxy-4-[1 S-(1,4,6/5)-5,6-dihydroxy-3-hydroxymethyl-4-O-α-D-glycopyranosyl-(1→4)-cyclohex-2-en-1-ylamino]-α-D-glycopyranosyl}-(1→4)-O-α-D-glucopyranosyl-(1→4)-D-glucopyranose of the conformational structural formula:

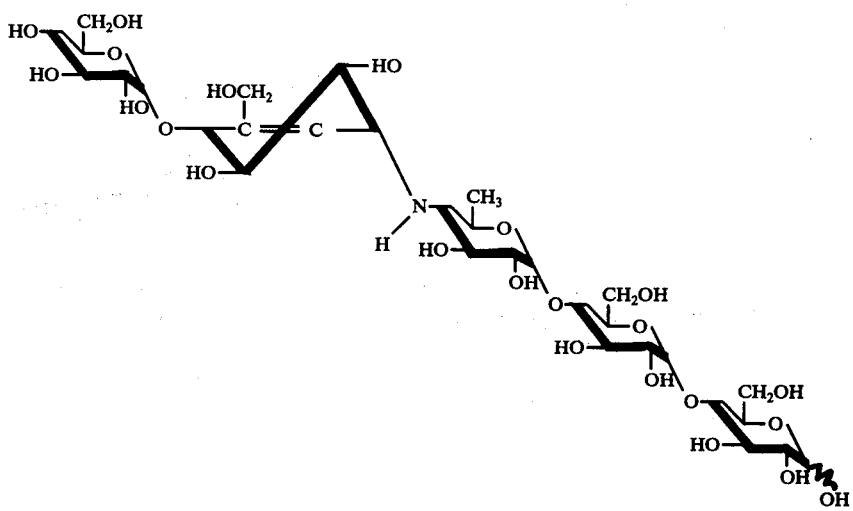

These isomers show $R_{glucose}$ values of 0.41 to 0.46 on F 1500 plates using 50:30:20 n-butanol:ethanol:water. The presence of the isomer having the structure shown in Formula VI can be shown by analysis of the products of hydrogenolytic degradation using palladium on charcoal as discussed in greater detail in Ser. No. 654,627.

The isomeric compounds of Formulas V and VI can be separated by chromatography on an acidic ion exchange resin with 0.025 N hydrochloric acid as an eluant.

The higher members of the series containing 4 to 8 glucose units have molecular weights of from 969 to 1617. On acid hydrolysis of these higher members, the lower components can, in each case, be detected as intermediate products together with glucose and maltose. Thin layer chromatography using 50:30:20 n-butanol:ethanol:water, on F 1500 silica gel plates give $R_{glucose}$ values of 0.30–0.34 (predominantly four glucose units); 0.21–0.23 (predominantly five glucose units); 0.14–0.16 (predominantly six glucose units); and 0.09–0.11 (predominantly seven glucose units).

As in the case of the lower members of this series, total acid hydrolysis yields "component I" and glucose in discrete molar ratios, specifically 1:4, 1:5, 1:6, 1:7 and 1:8, (the percentages of glucose being 74.4%, 79.7%, 83.3%, 86.5% and 89.1%, respectively).

Upon thin layer chromatography using F 1500 silica gel plates with 45:35:20 n-butanol:ethanol:water as the solvent, the following $R_f$ values are observed upon threefold development:

| Ratio Glucose:Compound I | Standard | $R_f$ value |
| --- | --- | --- |
|  | Glucose | 0.77 |
|  | Maltose | 0.65 |
|  | Maltotriose | 0.51 |
|  | Maltotetraose | 0.39 |
|  | Maltopentaose | 0.27 |
| 4:1 |  | 0.25 |
|  | Maltohexaose | 0.21 |
| 5:1 |  | 0.18 |
|  | Maltoheptaose | 0.15 |
| 6:1 |  | 0.13 |
|  | Maltooctaose | 0.11 |
| 7:1 |  | 0.09 |

| Ratio Glucose:Compound I | Standard | $R_f$ value |
|---|---|---|
| 8:1 | | 0.07 |

Similarly, catalytic hydrogenation demonstrates that some, but not all, of the glucose units of these higher members are bound through the 4-position of the cyclohexane group.

Since these compounds contain oligoglucosidic linear chains with 1→4 linkages, they can serve as substrates for certain carbohydrate degrading enzymes. The range of enzymes is obviously limited to those which are not substantially inhibited by the compounds. Bacterial and fungal α-amylases can however be used to degrade any oligoglucosidic chain containing 2 or more glucose units and yielding compounds of lower molecular weight and inert saccharide fragments such as maltose and maltotriose. This degradation procedure is further proof for 1→4 α-linkage. Compounds containing 4 to 8 glucose units are also degradable to some extent by β-amulase. Since β-amylase splits off maltose units from the non-reducing end of a glucose chain having 1→4 α-linkages, careful analysis of β-amylase degradation products yields valuable information on any oligoglucosidic substituent bound to the 4-position of the cyclohexane ring, specifically its chain length, and the number of glucoses in the chain attached to the bisdesoxyglucose; i.e., the reducing end of the compound. The compounds containing 4, 5, 6, 7 or 8 glucose units are however not completely degradable by β-amylase, the resistance of some fragment of the compound apparently being due to insufficient structural requirements for β-amylase attack.

The results of β-amylase degradation can be summarized as follows:

| No. of glucose units in starting material | No. of glucose units in degradation product(s) | Maltose units removed |
|---|---|---|
| 4 | 4 | 0 |
|   | 2 | 1 |
| 5 | 5 | 0 |
|   | 3 | 1 |
| 6 | 6 | 0 |
|   | 4 | 1 |
|   | 2 | 2 |
| 7 | 7 | 0 |
|   | 5 | 1 |
|   | 3 | 2 |
| 8 | 8 | 0 |
|   | 6 | 1 |
|   | 4 | 2 |
|   | 2 | 3 |

In each case some starting material, possibly isomeric, is recovered. As to that material which is degraded, it should again be emphasized that the β-amylase will successively remove only maltose units and only from the non-reducing end of the oligosaccharide. Consequently while not wishing to be bound by any theory and while the precise structure of these higher compounds has not been fully elucidated, it appears the compounds containing 4, 5, 6, 7 and 8 glucose units include derivatives of the lower members of Formula IVA and IVB containing chains of 2, 3, 4 and 6 glucose units joined 1→4 α to each other with the last being joined 1α to the 4-position of the cyclohexane ring.

Methylation of the compounds with methyliodide/sodium hydride in dimethyl sulfoxide, subsequent total hydrolysis and derivatization, followed by gas chromatographic analysis yields only the 2,3,6-trimethyl glucose derivative, so that the glucose units are necessarily joined 1→4 in an exclusively linear structure. A second methylation product, which is found to a varying degree or under certain circumstances not at all, is the 2,3,4,6-tetramethyl derivative. The existence of this derivative and its molar ratio to the trimethyl derivative is dependent on the substituent attached to the cyclohexane ring.

While not wishing to be bound by any theory, it appears that these amino-sugars have a desirable effect on meat:fat ratios by reason of their ability to inhibit glycoside hydrolases.

It is known that hyperglycaemias occur after ingestion of carbohydrate material. These hyperglycaemias are due to a rapid degradation of the carbohydrates by glycoside-hydrolases (for example salivary and pancreatic amylases, maltases and saccharases) in accordance with the following equation:

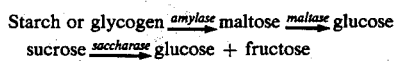

Starch or glycogen $\xrightarrow{amylase}$ maltose $\xrightarrow{maltase}$ glucose sucrose $\xrightarrow{saccharase}$ glucose + fructose With adipose animals, alimentary hyperglycaemia frequently leads to a particularly powerful secretion of insulin which in turn leads to increased fat synthesis and reduced fat degradation. Following such hyperglycaemias, hypoglycaemia frequently occurs in adipose animals due to the insulin secretion. The amino-sugars utilized in the present invention substantially reduce alimentary hyperglycaemia, hyperinsulinaemia and hypoglycaemia. This can be observed after feeding rats and/or humans with starch, sucrose or maltose. The compound thus accelerate the passage of carbohydrates through the stomach and inhibit the absorption of glucose from the intestine. The conversion of carbohydrates into lipids of the fatty tissue and the incorporation of alimentary fat into the fatty tissue depots is accordingly reduced or delayed.

The inhibitory profile of the present compounds against relevant enzymes can be readily observed in the following tests.

In Vitro Amylase Test

One amylase inhibitor unit (I AIU) is defined as the amount of inhibitor which inhibits two amylase units to the extent of 50%. One amylase unit (AU) is the amount of enzyme which under the test conditions specified below splits 1 μequivalent of glucoside bonds in the starch per minute. The μequivalents of split bonds are determined colorimetrically as μequivalents of reducing sugars formed, using dinitrosalicylic cid, and are quoted as μequivalents of maltose equivalents, using a maltose calibration curve. To carry out the test, 0.1 ml of amylase solution (20–22 AU/ml) are mixed with 0–10 μg of inhibitor or 0–20 μl of the solution to be tested in 0.4 ml of 0.02 M sodium glycerophosphate buffer/0.001 M CaCl$_2$, pH 6.9, and the mixture is equilibrated for 10–20 minutes in a water bath at 35° C. The mixture is then incubated for 5 minutes at 35° C with 0.5 ml of a 1% strength starch solution which has been pre-warmed to 35° C (soluble starch No. 1,252 from Merck, Darmstadt), and thereafter 1 ml of dinitrosalicylic acid reagent (according to P. Bernfeld in Colowick-Kaplan, Meth. Enzymol., Volume 1, page 149) is added. To develop the color, the batch is heated for 5 minutes on a boiling water bath and then cooled, and 10 ml of distilled water are added. The extinction at 540 nm is measured against a correspondingly made-up blank without amylase. For evaluation, the amylase activity which is still effective after addition of inhibitor is read off a previously recorded amylase calibration curve and the percentage inhibition of the amylase employed is calculated therefrom. The percentage inhibition is plotted as a function of the quotient $$\frac{\mu g \text{ of inhibitor } +}{AU\ ++}$$

+ relative to solid
++ AU in non-inhibited batch of the same series and the 50% inhibition point is read off the curve and converted to AIU/mg of inhibitor.

In Vitro Saccharase Test

One saccharase inhibitor unit (SIU) is defined as the amount of inhibitor which inhibits two saccharase units to the extent of 50%. One saccharase unit (SU) is the amount of enzyme which under the test conditions specified splits 1 $\mu$mol of sucrose to glucose and fructose per minute. The $\mu$mols of glucose formed are determined quantitatively by means of the glucose oxidase reaction under conditions under which a further splitting of the sucrose by the saccharase no longer takes place. To carry out the test, 0.05 ml of solubilized saccharase [from the mucous membrane of the small intestine of the pig, according to B. Borgström, A. Dahlquist, Acta Chem. Scand. 12, (1958), page 1,997], diluted with 0.1 M sodium maleate buffer of pH 6.0 to a SU content adjusted to 0.12 SU is mixed with 0–20 $\mu$g of inhibitor or 0–20 $\mu$l of the solution to be tested and brought up to 0.1 ml with 0.1 M sodium maleate buffer of pH 6.0. The mixture is equilibrated for 10 minutes at 35° C and 0.1 ml of an 0.05 M sucrose solution in 0.1 m sodium maleate buffer of pH 6.0, pre-warmed to 35° C, is then added. The mixture is incubated for 20 minutes at 35° C, the saccharase reaction is stopped by addition of 1 ml of glucose oxidase reagent, and the incubation is continued for a further 30 minutes at 35° C. (The glucose oxidase reagent is prepared by dissolving 2 mg of glucose oxidase, Boehringer, No. 15,423, in 100 ml of 0.565 M tris-HCl buffer of pH 7.0 and subsequently adding 1 ml of detergent solution (2 g of Triton $\times$ 100 + 8 g of 95% strength analytical grade ethanol), 1 ml of dianisidine solution (260 mg of o-dianisidine.2HCl in 20 ml of H$_2$O) and 0.5 ml of 0.1% strength aqueous peroxidase solution, Boehringer, No. 15,302). Thereafter, 1 ml of 50% strength H$_2$SO$_4$ is added and a measurement carried out at 545 nm against a corresponding blank. To evaluate the results, the percentage inhibition of the saccharase employed is calculated and converted to SIU/g or SIU/liter from the 50% inhibition point, using a glucose calibration curve.

In Vitro Maltase Test

One maltase inhibitor unit (MIU) is defined as the amount of inhibitor which inhibits two maltase units to the extent of 50%. One maltase unit (MU) is the amount of enzyme which in one minute, under the test conditions specified below, splits 1 $\mu$mol of maltose into 2 $\mu$mol of glucose. The $\mu$mol of glucose formed are determined quantitatively by means of the glucose oxidase reaction under conditions such that further splitting of maltose by the maltase no longer takes place. To carry out the test, 0.05 ml of solubilized maltase [from the mucous membrane of the small intestine of the pig, according to B. Borgstrom, A. Dahlquist, Acta Chem, Scan. 12, (1958), page 1,997], diluted with 0.1 M sodium maleate buffer of pH 6.0 to 0.060–0.070 MU is mixed with 0–20 $\mu$g of inhibitor of 0–20 $\mu$l of the solution to be tested and made up to 0.1 ml with 0.1 M sodium maleate buffer of pH 6.0. The mixture is equilibrated for 10 minutes at 35° C and 0.1 ml of an 0.05 M maltose solution in 0.1 M sodium maleate buffer of pH 6.0, pre-warmed to 35° C, is then added. The mixture is incubated for 20 minutes at 35° C and the maltase reaction is stopped by addition of 1 ml of the glucose oxidase reagent described above, and the incubation is continued for a further 30 minutes at 35° C. Thereafter, 1 ml of 50% strength sulfuric acid is added and a measurement carried out at 545 nm against a corresponding blank.

To evaluate the results, the percentage inhibition of the maltase employed is calculated and converted to MIU/g or MIU/liter from the 50% inhibition point, using a glucose calibration curve.

The results of the in vitro enzyme inhibition tests for specific individual compounds and discrete ranges of higher members of these amino-sugars are discussed in greater detail in Ser. No. 654,627.

Briefly, in vitro inhibitory activity towards pancreas-$\alpha$-amylase increases greatly with increasing molecular weight in the series, the compounds with 5 to 7 glucose units showing a 100-fold greater inhibition in vitro than the compounds with 1 or 2 units. Saccharase inhibition is most pronounced for the derivative having two units, the derivative having one glucose unit showing inhibition only half as much, and the higher member showing further decreases in saccharase inhibition. In vivo, the activity in saccharase inhibition (the sucrose overfeeding test) runs approximately parallel to the specific inhibitory activity found in vitro. On the other hand, in vivo starch digestion (the starch feeding test) for the compounds having 1, 2 or 3 glucose units unexpectedly increases 10 to 40-fold, in comparison to the amylase inhibition in vitro. Surprisingly the in vivo inhibition of starch digestion by the compounds having 1, 2 and 3 glucose units is much higher than would be expected from in vitro amylase inhibition and does not follow the anticipated pattern. Thus while the level of saccharase inhibition is a characteristic function of molecular weight, both in vitro and in vivo, and amylase inhibition is conversely a direct function of molecular weight in vitro, in vivo inhibition of starch digestion does not decrease with decreasing molecular weight but surprisingly remains constant.

The compound having 4 glucose units also shows high in vitro activity as an $\alpha$-amylase inhibitor and those having 5 and 6 units, while somewhat lower, exhibit considerably higher specific inhibitor activities than found with any previous preparation. There is a decrease in inhibitor activity with increasing molecular weight, as in the case of the compounds having 7 and 8 glucose units, although these still show considerable inhibition. In vitro saccharase inhibition appears to be an inverse function of molecular weight. The compound with 4 glucose units exhibits about 1/10 of the specific activity of the compound having two glucose units whereas the saccharase inhibitory activity of the compound with eight glucose units is only marginal.

The following examples will serve to further typify the nature of this invention. Examples 1–13 describe the preparation of various amino-sugars utilized in the invention and reference is made to Ser. No. 654,627 for further details on these procedures. In these examples, representative ion exchange resins which can be used include AMBERLITE IRA 410 Cl⁻ (anion exchanger);

AMBERLITE IRC 120 (H+ form) (strongly acid ion exchanger); AMBERLITE (HCO$_3^-$ form) (anion exchanger); AMBERLITE IRA 410 OH$^-$ (strongly basic ion exchanger); AMBERLITE IRC 50 H+ (weakly acid cation exchanger) and DOWEX 50 WX4 H+ (strongly acid ion exchanger).

The microorganisms used herein have been deposited with the American Type Culture Collection under the following numbers:

| Strain | ATCC No. |
|---|---|
| SE 50 (CBS 961.70) | 310 42 |
| SE 18 (CBS 957.70) | 310 41 |
| SE 82 (CBS 615.71) | 310 45 |
| SE 50/13 (CBS 614.71) | 310 43 |
| SE 50/110 (CBS 674.73) | 310 44 |

EXAMPLE 1

A glass fermenter filled with 8 liters of nutrient solution containing 5.0% of starch, 1.0% of yeast extract and 0.2% of K$_2$HPO$_4$ is inoculated with a 3 day old shaken flask culture of the strain SE 50/13 (CBS 614.71) and the mixture is incubated with intensive stirring and aeration for 3 days at 28° C, giving a culture broth containing 105,000 AIU/ml.

6 liters of this culture broth are cooled to 20° C, the pH is adjusted to 2.5 with half-concentrated HNO$_3$, 30 g of Carboraffin active charcoal are added and the mixture is stirred for 10 minutes. It is then centrifuged at 10,000 rpm for 15 minutes and the clear light yellow supernatant liquid is neutralized with NH$_3$ and then concentrated to 500 ml. The 500 ml of concentrate were stirred for 45 minutes with 200 g of Amberlite IRA 410 Cl$^-$, the latter was filtered off and the filtrate was treated with 4/5 of its volume (= 400 ml) of methanol in order to precipitate the bulk of the higher-molecular starch degradation products (together with active charcoal residues still present). The mixture is centrifuged for 5 minutes at 5,000 rpm. The 850 ml of supernatant liquid are added dropwise to 4 liters of dry spirit, with intensive stirring. The white flocculent precipitate is filtered off, washed 3 times with dry spirit and twice with ether and dried in vacuo at 50° C. Yield: 36 g of a white powder containing 10 × 10$^6$ AIU/g. This preparation is referred to below in several locations.

EXAMPLE 2

A. If a 1 liter Erlenmeyer flask containing 120 ml of a nutrient solution consisting of 4% of starch, 2.4% of glucose, 0.9% of casein hydrolysate and 0.9% of yeast extract, pH adjusted to 7.6 with NaOH, mixed with 0.4% of CaCO$_3$ and sterilized for 30 minutes at 121° C, is inoculated with 3 ml of a pre-culture of the strain SE 82 (CBS 615.71), grown in a nutrient solution consisting of 2% of starch, 1% of glucose, 0.5% of casein hydrolysate and 1% of yeast extract, pH adjusted to 7.2 with NaOH, treated with 0.4% of CaCO$_3$ and sterilized for 30 minutes at 121° C, and the whole is incubated for 5 days at 28° C on a rotary shaking machine, a culture solution containing 122,000 AIU/ml is obtained. For working up, the mycelium is separated from the combined culture solutions by centrifuging at 12,000 rpm, 300 ml of the culture filtrate are brought to pH 2.5 with half-concentrated HNO$_3$ and the mixture is stirred for 10 minutes with 2.5 g of analytical grade active charcoal. After separating off the charcoal at 12,000 rpm, the solution is neutralized to pH 6 with 10 N KOH, 300 ml of methanol are added, the mixture is allowed to stand briefly and the precipitate is removed at 12,000 rpm. If the supernatant liquid is now added dropwise to 3 liters of ethanol and the precipitate is isolated, after brief standing, by centrifuging at 12,000 rpm and is washed twice with absolute ethanol and once with ether and dried in vacuo, 2.23 g of a product containing 7.45 × 10$^6$ AIU/g are obtained, which contains more than 95% of compounds having from 4 glucose units upwards.

B. If a 1 l Erlenmeyer flask with 120 ml of a nutrient solution of composition 3.5% of glucose, 2% of starch 0.5% of casein hydrolysate, 1.3% of yeast extract, 0.3% of CaCO$_3$ and 0.3% of K$_2$HPO$_4$, adjusted to pH 7.8 before sterilization and sterilized for 30 minutes at 121° C, is inoculated with 6 ml of a pre-culture of the strain SE 50/110 (CBS 674.73) in a nutrient solution consisting of 3% of soya flour, 3% of glycerol and 0.2% of CaCO$_3$ and the mixture is incubated for 3-4 days on a rotary shaking machine at 24° C, a culture solution which contains 153,000 AIU/ml and 12,000 SIU/liter is obtained.

1 liter of culture solution was adjusted to pH 2.5 with HNO$_3$ and the mixture was stirred for 10 minutes with 5 g of active charcoal and then centrifuged for 30 minutes at 5,000 rpm. It was then neutralized by adding 25 g of Amberlite IRA 410 (OH$^-$ form). The neutral supernatant liquid was concentrated to 100 ml on a rotary evaporator, mixed with 100 ml of methanol and filtered. The filtrate was stirred into 2 liters of dry spirit and the precipitate which separated out was filtered off, washed 3 times with acetone and ether and dried in vacuo.

Yield 14 g of a white powder containing 5 × 10$^6$ AIU/g and predominantly containing compounds having from 4 glucose units upwards.

C. If the procedure of Part A. is followed but with the addition of 0.5% starch, a culture broth containing 40,000 AIU and 184 SIU/ml is obtained after 4 days' fermentation. The culture broth contains a mixture of compounds of the invention having from one glucose unit upwards.

EXAMPLE 3

A. If a 1 liter Erlenmeyer flask which contains 120 ml of nutrient solution of composition 3% of glucose, 0.6% of casein hydrolysate, 1.6% of yeast extract, 0.3% of CaCO$_3$ and 0.3% of K$_2$HPO$_4$, pH adjusted to 7.8 with KOH before sterilization, is inoculated with a pre-culture of the strain SE 50/110 (CBS 674.73) according to Example 3 and incubated for 4 days at 24° C on a rotary shaking machine, a culture broth of 10,800 SIU/liter, which predominantly contains the compound of the invention having one glucose unit, is obtained.

5 Liters of culture filtrate, separated from the mycelium at 13,000 rpm, were adjusted to pH 2.5 with half-concentrated HNO$_3$ and stirred for 15 minutes with 55 g of active charcoal ("Merck") and 200 g of Clarcel. After removing the solids by suction filtration, the filtrate was neutralized to pH 7 with concentrated ammonia and the solution was concentrated to 1.5 liter and precipitated with a five-fold amount of ethanol. The resulting flocculent precipitate was separated off using a continuous-flow rotor at 12,000 rpm and the yellowish supernatant liquid was concentrated to 150 ml and centrifuged at low speed to separate off minor proportions of undissolved material. 50 ml of this solution were charged onto a column filled with Amberlite IR-120 (H+ form) (30 × 300 mm; 30 ml of H$_2$O per hour). After a total of 300 ml of eluate, which contains inert saccharides and a proportion of non-adsorbed components having an inhibiting action, had been collected, the exchanger was transferred into a beaker with about 400 ml of $H_2O$ and concentrated ammonia was added, while stirring, until the pH had reached a value of 11.5. After stirring for a further 30 minutes, the exchanger was separated off, the liquid was concentrated to 1/20 of its volume and filtered through a column (20 × 150 mm) containing Amberlite IRA-410 ($HCO_3^-$ form) and about 500 ml of eluate were collected at a flow speed of 30 ml/hour; the eluate was concentrated and after lyophilization gave 1.3 g of crude product.

For further purification, the crude product was fractionated on polyacrylamide gel (Bio-Gel P-2), 100–200 mesh (Bio-Rad, Munich). A column of 50 mm diameter and 450 mm length was used for this purpose and was operated with $H_2O$ at a flow speed of 40 ml per hour, fractions of 10 ml each being collected. All fractions were tested by means of the anthrone test for carbohydrates and by means of the saccharase inhibition test for components having an inhibiting action. The fractions containing saccharase inhibitor were further examined by thin layer chromatography, in accordance with Example 1, for their content of individual components. The fractions which contained the compound having one glucose unit were combined, concentrated and lyophilized. 35 mg of material showing $0.3 \times 10^6$ AIU/g and 30,000 SIU/g, were obtained.

B. If 1 l Erlenmeyer flasks each containing 120 ml of a nutrient solution of composition 5% of starch, 1% of yeast extract and 0.2% of $K_2HPO_4$ are each inoculated with 2 ml of a pre-culture according to Example 3A and incubated for 3 days at 28° C, culture solutions with the following yield of amylase inhibitor are obtained:

| Strain | AIU/ml |
| --- | --- |
| SE 50 (CBS 961.70) | 37,000 |
| SE 50/13 (CBS 614.71) | 109,000 |
| SE 50/110 (CBS 674.73) | 53,500 |

The mixture consists predominantly of a mixture of compounds with four or more glucose units.

C. If 1 l Erlenmeyer flasks each containing 120 ml of nutrient solution of composition 1.3% of maltose, 3.5% of glucose, 0.5% of casein hydrolysate, 1.3% of yeast extract, 0.3% of $CaCO_3$ and 0.3% of $K_2HPO_4$ are each inoculated with 2 ml of a pre-culture according to Example 3A, the following yields are obtained after 4 days' incubation with various strains on rotary shaking machines at 24° C:

| Strain | SIU/ml | AIU/ml |
| --- | --- | --- |
| SE 50 (CBS 961.70) | 25 | 580 |
| SE 50/13 (CBS 614.71) | 14.8 | 1,460 |
| SE 50/110 (CBS 674.73) | 57.9 | 755 |

The products consist predominantly of a mixture of compounds having four or less glucose units.

EXAMPLE 4

If a fermenter containing 100 l of nutrient solution of composition 3.5% of glucose, 2.5% of dry powdered malt extract, 0.5% of casein hydrolysate, 1.3% of yeast extract, 0.3% of $CaCO_3$, 0.3% of $K_2HPO_4$ and 0.1% of anti-foaming agent is inoculated with 5 l of a pre-culture according to Example 3A and incubated for 5 days at 24° C with stirring and aeration, a culture solution of 73,000 SIU/l is obtained, which predominantly contains the compound of the invention with two glucose units.

A 90 liter fermentation batch together with the mycelium is adjusted to pH 2.5 on a pH meter by means of concentrated $HNO_3$ and 900 g (= 1%) of active charcoal (Merck) are added while stirring in order to adsorb the bulk of the dyestuffs formed. The mixture is stirred for 15 minutes, the mycelium and the bulk of the charcoal were separated off on a centrifuge at 3,000 rpm and the supernatant liquid, with addition of 3 kg of Clarcel, is finally filtered through a pressure filter. 65 l of yellow-brown, clear filtrate of SIU content 60,000 SIU/liter are obtained.

The filtrate is adjusted to pH 7 with concentrated $NH_3$ and stirred with 1,300 g (2%) of active charcoal (Merck) for 30 minutes in order to adsorb the active substance. The mixture is filtered through a pressure filter and the active charcoal sediment was washed 3 times with 10 liters of distilled water. The charcoal is then thoroughly pressed dry and stirred with 3 times 4 liters of 50% strength acetone at pH 2.5, in each case for 15 minutes, so as to desorb the active substance from the charcoal. The acetone desorbates are combined after removing the charcoal by filtration. The combined desorbate is concentrated to 250 ml on a rotary evaporator, an equal volume (250 ml) of methanol is added and the mixture is filtered through a folded filter. The filtrate (480 ml) is added dropwise to 5 liters of acetone, with vigorous stirring. The precipitate which separated out is filtered off and washed 3 times with acetone and ether. It is then dried in vacuo at 35° C. Yield 230 g of crude product containing 8,500 SIU/g.

25 g of the above crude product are dissolved in 1 liter of $H_2O$ and stirred with 300 g of Dowex 50 WX 4 H+ (200–400 mesh) for 30 minutes. The resin is filtered off and rinsed 3 times with 2 liters of 0.001 N HCl. The washed Dowex is then suspended in 500 ml of $H_2O$ and the suspension adjusted to pH 9.0 on a pH meter by addition of 25% strength $NH_3$. Thereafter 2 further desorptions are carried out, each with 500 ml of 0.6% strength $NH_3$ and the desorbates are combined and concentrated to 100 ml on a rotary evaporator. To decolorize this concentrate, it is stirred for 5 minutes with 2 g of DEAE-cellulose (Schleicher and Schüll, No. 02035, 0.6 milliequivalent/g), and then centrifuged. The light yellow supernatant liquid is mixed with an equal volume (100 ml) of methanol and the mixture is then added dropwise to 2 liters of acetone, with intensive stirring. The precipitate is filtered off, washed with acetone and ether and dried in vacuo at 35° C.

For additional fine purification, the 4.0 g of inhibitor are gel-filtered, in 0.5 g portions, through Biogel P-2. For this purpose, each 0.5 g of the preparation is dissolved in 10 ml of $H_2O$ and the solution was charged onto a Biogel P-2 column (200–400 mesh, Bio-Rad) of 5 cm diameter and 95 cm length. The column is developed in water at a flow rate of 80 ml/hour. 12 ml fractions are collected. For all fractions, the total carbohydrate content (in the form of the anthrone test, as an extinction at $E_{620}$) and the content of saccharase inhibitor and amylase inhibitor is determined. In addition, the fractions are tested by thin layer chromatography (enzyme inhibition coloration according to Example 1).

The fractions containing the compounds with 4–6 glucose units are combined, concentrated to 10 ml in vacuo and precipitated by dropwise addition to 200 ml of ethanol. The precipitate is centrifuged off, washed with acetone and ether and dried in vacuo; yield from 4.0 g of crude inhibitor: 0.2 g of compounds having 4 to 6 glucose units with activity of $17.5 \times 10^6$ AIU/g and 8,500 SIU/g. The fractions containing the compound with 3 units are worked up in the same manner, the precipitation being carried out with 200 ml of acetone; yield from 4.0 g of crude inhibitor: 0.1 g of compound of the invention with 3 units, containing $1.4 \times 10^6$ AIU/g and 21,000 SIU/g. 0.9 g of the compound of the invention with 2 units containing $0.3 \times 10^6$ AIU/g and 68,000 SIU/g is isolated from the fractions (precipitation with acetone) containing the compound having 2 glucose units.

EXAMPLE 5

To isolate the compounds with 5–7 glucose units the starting material used can be, for example, a preparation such as described in Example 1. For this purpose, 30 g of the preparation according to Example 1 were dissolved in 250 ml of $H_2O$. The conductivity of the resulting solution was 10 mS.cm$^{-1}$ and the pH was 5.5. The solution was desalinated by adding 60 g of Amberlite IRC 50 H+ (weakly acid cation exchanger which only binds traces of the amino-sugar derivatives from aqueous solution) and 20 g of Amberlite IRA 410 OH− and stirring for 20 minutes. The filtrate (conductivity 0.5 mS, pH 3.5) was adjusted to pH 3.0 with 1 N HCl (conductivity 0.6 mS). This solution was pumped at the rate of 42 ml/hour through a column filled with Dowex 50 W $\times$ 4, 200–400 mesh. (H+) ($\phi$ 2.5 cm, height 40 cm, equilibrated in 0.001 N HCl) and the Dowex was then rinsed with 2 l of 0.001 N HCl. After washing the column, elution was carried out with 1.2% strength aqueous ammonia and 10 ml fractions were collected. The fractions having an inhibiting action were combined, the ammonia was stripped off in vacuo and the solution was then concentrated in vacuo to 30 ml. The product was precipitated in dropwise addition to 600 ml of dry spirit and the precipitate was filtered off, washed with alcohol and ether and dried in vacuo. Yield 4.4 g, containing $26.5 \times 10^6$ AIU/g.

0.5 g portions were subjected to a fine purification by application to a preparative Biogel P-2 column, as described in Example 4, and development. The fractions which according to a thin layer chromatogram (amylase inhibition coloration) contain compounds with 5 to 7 glucose units were combined, concentrated in vacuo and precipitated with dry spirit as described above. Yield from 0.5 g of crude product: 0.2 g of amino-sugar derivatives with 5 to 7 glucose units containing $30 \times 10^6$ AIU/g and 2,500 SIU/g.

EXAMPLE 6

200 g of a preparation as described in Example 1 were dissolved in 940 ml of distilled water and 60 ml of concentrated $H_2SO_4$ and the mixture was warmed under reflux for 4 hours (internal temperature: 98°–100° C; oil bath temperature: 140° C). 10 g of active charcoal (Merck Art. 2186) were added to the cooled blackbrown solution and the mixture was stirred for 1 hour. The active charcoal was then filtered off and washed with water and the filtrate was adjusted to pH = 7 to 8 with about 250 ml of 10 N KOH. The solution was stirred for 1 hour with 50 g of active charcoal. The charcoal was filtered off and washed with 2 l of water and the filtrate was discarded. For desorption, the charcoal was digested overnight with 2 l of 30% strength alcohol. Finally, the charcoal was filtered off and the alcoholic solution was concentrated on a rotary evaporator. Residue: 6.2 g. This crude product (6.2 g) was dissolved in 500 ml of water and the solution was gently stirred with 30 g of Amberlite IR 120 (H+ form) for 1 hour. The exchanger was filtered off and washed with distilled water until the filtrate was neutral and free from glucose. The exchanger was then stirred overnight with 15 ml of 25% strength $NH_3$ in 1,000 ml of $H_2O$, separated off and discarded. The filtrate was concentrated on a rotary evaporator. Residue: 3.7 g.

For further purification, a chromatography on cellulose was carried out. 4.5 g of the material desorbed from the exchanger were applied to a 1 m long and 2.5 cm wide column filled with cellulose. The running agent used was initially 5:1 ethanol/$H_2O$, and 3:1 ethanol/$H_2O$ was initially used to eluate the compound of the invention with $n = 1$. Fractions of 14 ml were collected at a drip speed of 20 drops per minute. The individual fractions were examined by thin layer chromatorgraphy. Fractions 47–85 gave, after concentration, 1.6 g of a compound of the invention with $n = 1$, exhibiting a pale brownish discoloration. The discoloring impurities were quantitatively insignificant. The compound with one glucose unit was obtained as a colorless resin if the purification step with a strongly acid ion exchanger was carried out on a column and not by the batch process.

EXAMPLE 7

200 g of a preparation as described in Example 1 were dissolved in 940 ml of distilled water and 60 ml of concentrated $H_2SO_4$ and the solution was warmed under reflux for ¼ hour (internal temperature: 98°–100° C; oil bath temperature: 140° C). 10 g of active charcoal (Merck, Art. 2186) were added to the cooled, blackbrown solution and the mixture was stirred for 1 hour. The active charcoal was then filtered off and washed with water and the filtrate was adjusted to pH = 7 to 8 with about 250 ml of 10 N KOH. The solution was stirred with 50 g of active charcoal for 1 hour. The charcoal was filtered off and washed with 2 l of water and the filtrate was discarded. For desorption, the charcoal was digested overnight with 2 l of 30% strength alcohol. Finally, the charcoal was filtered off and the alcoholic solution was concentrated on a rotary evaporator. Residue: 8.0 g.

The residue was taken up in 15 ml of $H_2O$ and applied to a column (height: 20 cm, diameter 2.4 cm) filled with 50 g of Amberlite IR 120 (H+ form). The solution was absorbed at 3 drops/minute and the column was rinsed with water (12 drops/minute) until all non-basic constituents had been removed. The basic products were then eluted from the column with 0.5 % strength $NH_3$ (12 drops/minute) and the aqueous solution was evaporated to dryness on a rotary evaporator. Residue: 4.1 g.

2 g of this residue were dissolved in a little water and applied to a column (height: 200 cm; $\phi$: 3.0 cm) filled with Sephadex G-15. The column was eluted with water. Fractions of 2 ml each were collected at a flow speed of 8 ml/hour. The individual fractions were examined by thin layer chromatography.. Fractions 85–94 gave 280 mg of the compound having 2 glucose units and a specific activity of 50,000 SIU/g.

EXAMPLE 8

If 2 g of a preparation as described in Example 1, in 60 ml of 20 mM sodium glycerophosphate buffer of pH 6.9, containing 1 mM of $CaCl_2$, are incubated with 1 g of $\alpha$-amylase from *Aspergillus* spec. (SERVA No. 13,418)

for 120 hours at 37° C with constant stirring and finally heated to 100° C for 5 minutes, and undissolved matter is centrifuged off at 4,000 rpm, lyophilization of the solution gives 1.9 g of a product is tested by thin layer chromatography and saccharase inhibition discoloration as described in Example 1, it is found that the compounds having an inhibiting action which are present are essentially the compounds of the invention with 2 and 3 glucose units.

EXAMPLE 9

If 2 g of a preparation as described in Example 1, in 30 ml of 20 mM acetate buffer of pH 4.8, are incubated with 1.25 mg of β-amylase from sweet potato (BOEHRINGER 15,471) for 120 hours at 37° C, with constant stirring and finally heated to 100° C for 5 minutes, and undissolved matter is centrifuged off at 4,000 rpm, lyophilization of the solution gives 1.5 g of a product with 1,800 SIU/g and $3.8 \times 10^6$ AIU/g. If this product is tested by thin layer chromatography and saccharase inhibition discoloration as described in Example 1, it is found that the compounds having an inhibiting action which are present are essentially the compounds of the invention with 2 and 3 glucose units.

EXAMPLE 10

If a 200 ml Erlenmeyer flask containing 25 ml of a nutrient solution of composition 0.1% $K_2HPO_4$, 0.2% of $(NH_4)_2SO_4$, 0.05% of $MgSO_4$, 0.05% of KCl, 0.01% of $FeSO_4$ and 2% of a preparation as described in Example 1 is inoculated with a spore suspension of the strain Asp. niger ATCC 11,394 and incubated at 28° C on a rotary shaking machine, the AIU concentration falls from 210,000 AIU/ml to 53,000 AIU/ml after 6 days and to 21,300 AIU/ml after 10 days. At the same time the SIU/ml content rises from 7.0 to 72 SIU/ml.

20 ml of a solution which has been incubated with the spore suspension for 10 days are centrifuged for 30 minutes at 3,000 rpm to separate off the mycelium. 15 ml of supernatant liquid (72,000 SIU/l) are desalinated by stirring for 30 minutes with 2 g of Amberlite IRC 50 H+ and 1 g of Amberlite IRA 410 OH− (conductivity less than 2 mSiemens). The mixture is filtered and the filtrate allowed to run at the rate of 5 ml/hour through a column (1 cm × 10 cm) of Dowex H+ equilibrated in 0.001 N HCl. The column is then rinsed with 200 ml of 0.001 N HCl. For desorption, 0.6% strength $NH_3$ solution is pumped through the column (10 ml/hour) and 5 ml fractions are collected. The fractions containing the saccharase-inhibiting activity are combined, concentrated to 2 ml on a rotary evaporator and mixed with 2 ml of methanol. This solution is adjusted to pH 3-4 and precipitated by adding it dropwise to 100 ml of acetone. The precipitate is filtered off, washed with acetone and ether and dried in vacuo. Yield: 26 mg containing 28,000 SIU/g and consisting of compounds with 2 and 3 glucose units. The isolation of the pure compound with 2 glucose units from this product is effected as described in Example 4 by gel filtration through a column containing Bio-Gel P-2. 7 mg of the compound with 2 glucose units of 60,000 SIU/g, are obtained.

EXAMPLE 11

2 Liters of culture filtrate obtained from a fermentation batch as described in Example 3A by centrifuging off the mycelium at 13,000 rpm and having an activity of 13,000 SIU/g were stirred with 500 g of a mixture of 2.5 parts of Amberlite IRC-50 (H+ form) and 1 part of Amberlite IRA-410 (OH− form) for 1 hour in order to reduce the salt content (conductivity of the culture filtrate: about 10 mS). The exchanger was separated off and the solution was concentrated to a little less than 100 ml and centrifuged for 15 minutes at 20,000 rpm to remove undissolved constituents. The supernatant liquid was made up to 100 ml; it now had a conductivity of 3.5 mS and was further purified by applying it to a column (55 × 400 mm) of P-cellulose (SERVA No. 45,130, pre-treated according to known methods and equilibrated in 5 mN ammonium phosphate buffer, pH 5.5). The abovementioned phosphate buffer served as the running agent; the flow rate was 90 ml/hour and fractions of 18 ml volume were collected.

After the fractions of the eluate had been tested for their carbohydrate content (by means of the anthrone test) and for their content of saccharase-inhibiting components (by means of the saccharase inhibition test), the fractions which in the anthrone test had proved almost free of carbohydrates and equally in the saccharase inhibition test had proved particularly active were combined (fractions 60–170), concentrated to 150 ml and filtered through a column (50 × 300 mm) containing Amberlite IRA-410 ($HCO_3^-$ form). For better control of the deionisation, the eluate was collected in fractions (10 ml per fraction in 20 minutes) and tested for carbohydrate (by means of the anthrone test: in each case virtually negative), for phosphate (by means of ascorbic acid-molybdate reagent: in each case negative) and for saccharase inhibition (by means of the enzyme inhibition test). The fractions having an inhibiting action (3–30) were combined, concentrated, lyophilized, redissolved and lyophilized so as to give 280 mg of crude inhibitor.

For further purification, the crude inhibitor was fractionated on Bio-Gel P-2 as described in Example 5. From the fractions which contained, pure, the compound with one glucose unit, 30 mg of a product with $0.3 \times 10^6$ AIU/g and 35,000 SIU/g were isolated after lyophilization. EXAMPLE 12

For the separation of the isomeric compounds having three glucose units, 10 g of a mixture of isomers dissolved in water were applied to a column (25 by 500 mm) filled with Dowex - 50 W X 4 (H+). The column was first washed with water until the eluate was neutral and then eluated with 0.025 N hydrochloric acid. Fractions of 3 ml each were collected and tested by thin layer chromatography. Thin layer chromatography was performed on silanized silica gel plates (Merck, German), with 100:60:40:2 ethylacetate:methanol:water:25% ammonia with threefold development. The isomer of Formula V travels a wider distance from the origin than does the isomer of Formula VI. Fractions 215 through 272 contains 6 g of the isomer of Formula VI. Fractions 288 through 294 containing 600 mg of the isomer of Formula V were pooled, neutralized with Amberlite IRA - 410 (OH−) and evaporated. The in vitro saccharase inhibiting activity of the isomer of Formula V isolated by this procedure is 19,000 SIE/g.

EXAMPLE 13

This Example illustrates how the compounds can be eluted from a cation exchanger under acid conditions.

A column of 1.5 cm. diameter is filled with 30 g (wet weight) of Dowex 50 W × 4, (H+) 200–400 mesh in 0.001 n HCL. Finally 500 ml. of mixed desorbate having 400,000 SIU/L, pH 2.5, 60% acetone, are pumped through the column in about 1 hour and washed finally with 500 ml of 0.001 N HCl. Under these conditions only trace activity is eluted. Finally desorption therefrom with 0.0125 N HCl was effected, the column eluate being monitored by conductivity or refractometry. The SIU content of the eluate was also tested. The active fractions 74–100 were combined and neutralized by the addition of Amberlite IRA 410 OH⁻, then reduced to 5 ml, reacted with 5 ml of methanol, and precipitated by dropping into 200 ml acetone. After washing with acetone and ether vacuum-drying was effected.

Yield 1 g of the compound with two glucose units with 65,000 SIU/g.

From the active initial fraction the compounds with 3 and 4 glucose units could be obtained.

This process of acid desorption therefore makes possible, in contrast to the alkaline desorption, fractionation of the individual amino sugar derivatives of this series. Subjecting material prepared as above having 4 to 8 glucose units to this process but simply lyophilizing the neutralized eluates, the individual higher fractions are obtained as follows:

4 glucose units = 67,000 AIU/mg
5 glucose units = 57,000 AIU/mg
6 glucose units = 42,000 AIU/mg
7 glucose units = 24,000 AIU/mg
8 glucose units = 5,000 AIU/mg The following examples illustrate animal feedstuffs with which the amino-sugar derivatives above defined can be combined:

EXAMPLE 14

Ready-Mixed Feedstuff For Poultry

The amino-sugar premix is prepared containing an amino-sugar in an amount corresponding to $5 \times 10^6$ AIU, for example 1,600 mg, together with 1 g of DL-methionine and sufficient soya bean flour to give 3.2 g of premix.

200 g of wheat, 340 g of maize, 360.3 g of shredded soya, 60 g of beef tallow, 15 g of dicalcium phosphate, 10 g of calcium carbonate, 4 g of iodized sodium chloride, 7.5 g of vitamin-mineral mixture and 3.2 g of the amino-sugar premix are carefully mixed to give 1 kg of feedstuff.

The vitamin-mineral mixture consists of 6,000 I.U. of vitamin $D_3$, 10 mg of vitamin E, 1 mg of vitamin $K_3$, 3 mg of riboflavin, 2 mg of pyridoxin, 20 mcg of vitamin $B_{12}$, 5 mg of calcium pantothenate, 30 mg of nicotinic acid, 200 mg of choline chloride, 200 mg of $MnSO_4 \times H_2O$, 140 mg of $ZnSO_4 \times 7H_2O$, 100 mg of $FeSO_4 \times 7H_2O$ and 20 mg of $CuSO_4 \times 5H_2O$.

EXAMPLE 15

A Mixed Feedstuff For Pigs 630 g of shredded feedstuff cereal (composed of 200 g of shredded maize, 150 g of shredded barley, 150 g of shredded oats and 130 g of shredded wheat), 80 g of fishmeal, 60 g of shredded soya, 58.8 g of tapioca meal, 38 g of brewer's yeast, 50 g of vitamin-mineral mixture for pigs (composition, for example, as for the chick feedstuff), 30 g of linseed oil cake meal, 30 g of maize gluten feedstuff, 10 g of soya oil, 10 g of sugar cane molasses and 2 g of active compound premix (composition, for example, as for the chick feedstuff) are carefully mixed to give 1 kg of feedstuff.

The above feedstuff mixtures are preferentially intended for raising and fattening chicks and pigs respectively but can also be used, in an identical or similar composition, for raising and fattening other animals.

As already mentioned, the amino-sugars can be used individually or in any desired mixtures with one another, and both the pure active compounds and the crude active compounds obtained from their process of preparation, optionally after a coarse purification, are employed. In the case of feedstuff preparations of particularly high dextrin content, for example sugar beets, it can be advisable to use amino-sugars having 1 to 8, preferably 1 to 3, glucose units, or to use mixtures of amino-sugars which contain a major proportion of the lower members. In the case of feedstuff preparations of particularly high starch content it can be advisable to use amino-sugars having a greater number of glucose units or to use mixtures which contain a major proportion of such higher members. The composition of active compound mixtures can be varied very extensively and is not to be regarded as critical.

The activity of the amino-sugars which can be used according to the invention can be demonstrated by the following examples:

EXAMPLE 16

Influence on the Development of Depot Fats

In Experiment 1, rats fed at set times were supplied with the active compound from Example 1 together with the feedstuff for 27 days. The epididymal and retroperitoneal (perirenal) fatty tissue weighed after this time showed that the active compound produces a decrease in, or reduced formation of, the epididymal and retroperitoneal fatty tissue, the effect being 15–40 percent, depending on the dose (see Table 1). The faecal excretion of starch was the same for all groups.

In Experiment 2, conventionally fed rats were supplied with the active compound from Example 4 together with the feedstuff for 28 days. The parametrial fatty tissue, weighed after this time, showed that the active compound produces a decrease in, or reduced formation of, the parametrical fatty tissue, the effect being 10–28 percent, depending on the dose (see Table 2).

Table 1

Fatty tissue weights in mg ± 1s *⁾ of rat, per 100 g of rat; *⁾ = standard deviation

| Tissue | Groups of experiments (for classification, see below) | | | |
|---|---|---|---|---|
| | I | II | III | IV |
| Retroperitoneal fat/rat | 662 ± 86 | 484 ± 206 | 449 ± 219 | 400 ± 188 |
| Retroperitoneal fat/100 g of rat | 361 (= 100%) | 271 (= 75%) | 274 (= 76%) | 226 (= 63%) |
| Epididymal fat/rat | 1473 ± 344 | 1213 ± 218 | 1288 ± 294 | 972 ± 237 |
| Epididymal fat/100 g of rat | 805 (= 100%) | 685 (= 85%) | 708 (88%) | 549 (= 68%) |

----- $p < 0.05$ ——— $p < 0.01$
relative to the group

Table 1-continued

Fatty tissue weights in mg ± 1s *) of rat, per 100 g of rat; *) = standard deviation

| Tissue | Groups of experiments (for classification, see below) | | | |
|---|---|---|---|---|
| | I | II | III | IV |
| (= percent with regard to control group (group I)) | | | | |

Classification of groups:
Group I = control
Group II = 0.010 mega-AIU of active compound/100 g of feedstuff
Group III = 0.050 mega-AIU of active compound/100 g of feedstuff
Group IV = 0.500 mega-AIU of active compound/100 g of feedstuff
Each group contained 12 animals

Table 2

Average bodyweight ± SD and average fatty tissue weights in mg ± SD after 28 days' supply of active compound from Example 4 with the feedstuff (n = 10)

| | Bodyweights | Fatty tissue weights |
|---|---|---|
| Control | 226 ± 13.0 g | 6,090 ± 2,472 mg |
| 1,000 SIU/100 g of feedstuff | 225 ± 6.8 g | 5,496 ± 1,067 mg |
| 3,000 SIU/100 g of feedstuff | 227 ± 9.1 g | 4,203 ± 1,225 mg |
| 10,000 SIU/100 g of feedstuff | 228 ± 18.0 g | 3,154 ± 1,107 mg |

- - - - $P < 0.05$
—— $P < 0.01$ against control

Tables 1 and 2 show clearly that the animals which received amino-sugars from Examples 1 and 4 deposit substantially less fat than the control animals which did not receive an active compound.

| Material and Methods for Experiments 1 and 2 | |
|---|---|
| Animal material in Experiment 1: | male Wistar rats/Winkelmann, SPF, 150–200 g |
| Animal material in Experiment 2: | female Wistar rats/Hagemann, SPF, 190–215 g |
| Feedstuff in Experiments 1 and 2: | full ration feedstuff with 50% of starch, tap water ad libitum |
| Animal accommodation in Experiments 1 and 2: | 6 rats/cage with wire bottoms and faeces tray |
| Feeding times in Experiment 1: | $8^{00}$ to $8^{30}$ and $16^{00}$ to $16^{30}$ |

Before the beginning of the experiment, the animals were rendered accustomed to this mode of feeding over 4 weeks.

| Feeding times in Experiment 2: | ad libitum |
|---|---|
| Weighing the organs in Experiments 1 and 2: | after bleeding the rats from the orbital vein plexus, stunning them by a blow on the head and cutting their throat, the epididyman, retroperitoneal and parametrial fatty tissue was prepared and weighed (accuracy: ± 0.2 mg). |

EXAMPLE 17

Reducing Fat Deposition and Improving Protein Deposition

In the course of fattening pigs, fed at set times, from approximately 60 to 150 kg live weight (requiring approximately 20 weeks), 5.0 mega-AIU of the amino-sugar from Example 1/kg of feedstuff (experimental group), or no active compound (control) were administered. After reaching a uniform final slaughtering weight of approximately 150 kg, all animals were killed and a series of data determined for assessing the quality of the carcasses.

After covariance-analytical correction of initial weight and final weight, and duration of the study, the following differences in the butchery criteria of the two groups were found:

Table 3

| Points of measurement | with active compound | without active compound |
|---|---|---|
| Formation of fat | | |
| Thickness of fat, withers, in cm | 5.43 ± 0.14 | 6.71 ± 0.12 |
| Thickness in fat, centre of back, in cm | 3.52 ± 0.08 | 4.15 ± 0.06 |
| Thickness of fat, loin, in cm | 4.71 ± 0.11 | 5.11 ± 0.09 |
| Ham, fat layer in kg | 5.03 ± 0.10 | 5.49 ± 0.09 |
| Formation of meat | | |
| Chop: fat-free centre portion of meat, in cm$^2$ | 50.4 ± 1.01 | 45.4 ± 0.84 |

The slaughtering results have shown that as a result of the use of the amino-sugars, the deposition of fat is reduced and the formation of meat (lean meat) is improved, for example by an increase in the proportion of meat over the area of the chop.

Material and Methods

Animal material:

From 5 litters, of equal age, of the white Belgian breed, 4 animals of equal strength (2 castrated males and 2 females) were selected in each case, and were in each case divided, in pairs, between the two experimental groups.

Accommodation:
Individual sties:
Feedstuff:

Commercially available pig fattening feedstuff with all nutrients and amino-sugars for optimum growth (in this context, see the mixed feedstuff recipe for pigs given earlier). Where the animals received the amino-sugar, the latter was given as a mixture with the feedstuff.

Feeding:

The feeding was carried out in accordance with the Rationstabelle der Deutschen Landwirtschafts-Gesellschaft (DLG) (Rations Table of the German Agricultural Association), that is to say the increase in the daily allocation of feedstuff was matched to the particular weight development of the average of the group. The feeding times were 8.00 a.m. and 8.00 p.m.

Experimental procedure:
a. Feeding experiment:

The experiment starts with approximately 60 kg live weight. Feeding corresponding to the weekly progress in weight. Weighing once weekly, always on the same day of the week, in the morning, before feeding. 3 animals (2 male, 1 female) of the experimental group were removed from the experiment in the 6th, 7th and 13th week, and 1 animal (female) of the control group was removed from the experiment, also in the 7th week of the experiment, in each case because of refusal of food. Dissection showed chronic pneumonia or a pneumonic infection. Taking the animals out of the experiment was therefore in no way related to their being fed the active compound.

b. Slaughtering experiment:

On reaching the predetermined final slaughtering weight of approximately 150 kg, all animals were killed by electrocution. The animals were gutted and both sides were weighted warm and then placed in a cold store for 24 hours. When they were cold, the sides were again weighed and the measurements summarized in the results were carried out. The measurements of the thickness of fat at the accurately defined points of measurement were carried out by means of a slide caliper and the layer of fat on the ham was carefully cut off and weighed. The area of meat of the chops was determined for all the animals in accordance with a standard method for assessing carcasses, developed for this purpose, by cutting a chop between the 13th and 14th rib. The chop surface was photographed to scale and the proportions of fat surface and meat surface were measured with a planimeter.

Evaluation:

The covariance-analytical correction of all the individual results was made with regard to the initial and final weight of the animals and the duration of the study.

What is claimed is:

1. A composition which when orally administered to animals influences the utilization of feed by reducing formation of fat and thereby increasing the meat:fat ratio of the animal in favor of a higher proportion of meat, said composition comprising at least one amino-sugar as herein defined in combination with an edible diluent or carrier, said amino-sugar chemically consisting of a 4,6-bidesoxy-4-(4,5,6-trihydroxy-3-hydroxymethylcyclohex-2-en-1-ylamino)-α-D-glucopyranose of the formula:

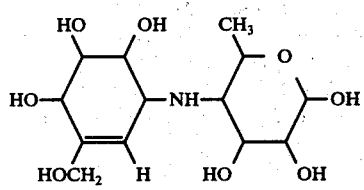

glycosidically linked with $n$ glucose residues, where $n$ is 1 to 40, which, when present in a polymeric chain of two or more glucose residues, are linked α-1:4, said amino-sugar yielding upon total acid hydrolysis the compound

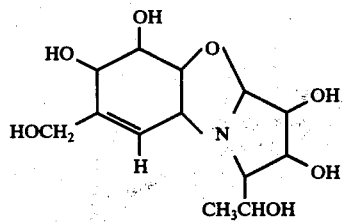

and glucose in a molar ratio of 1:$n$ where $n$ is as defined above.

2. A composition which when orally administered to animals influences the utilization of feed by reducing formation of fat and thereby increasing the meat:fat ratio of the animal in favor of a higher proportion of meat, said composition comprising at least one amino-sugar as herein defined in combination with an edible diluent or carrier, said amino-sugar having the conformational formula:

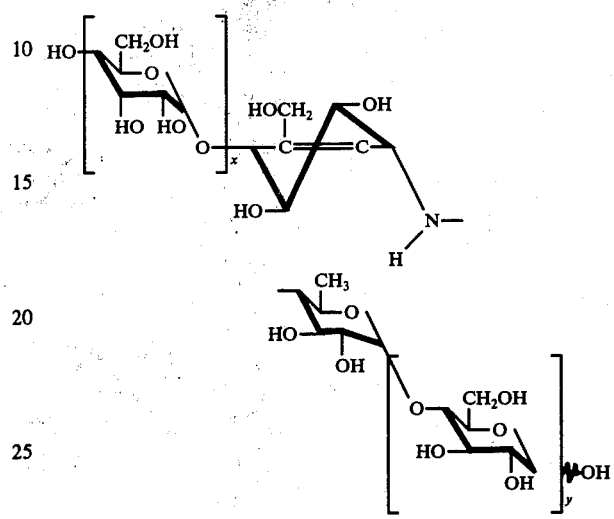

wherein
$y$ has a value of 1 to 8 and
$x$ has a value of from 0 to 7,
the sum of $y + x$ being from 1 to 8.

3. A composition according to claim 2 comprising a mixture of said amino sugars, the average value for the sum of $x$ and $y$ being from 1 to about 4.

4. A composition according to claim 3 comprising a single substantially pure amino sugar for which the sum of $x$ and $y$ is 1, 2, 3 or 4.

5. A composition according to claim 3 comprising at least one of said amino sugars wherein the sum of $x + y$ is 1.

6. A composition according to claim 5 wherein said amino sugar is O-{4,6-bisdesoxy-4-[1 S-(1,4,6/5)-4,5,6-trihydroxy-3-hydroxymethylcyclohex-2-en-1-ylamino]-α-D-glucopyranosyl}-(1→4)-D-glucopyranose of the conformational structural formula:

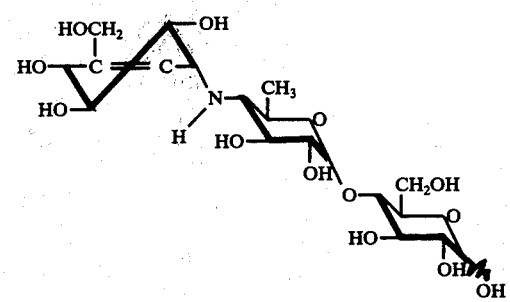

7. A composition according to claim 3 comprising at least one of said amino sugars wherein the sum of $x + y$ is 2.

8. A composition according to claim 7 wherein said amino sugar is O-{4,6-bisdesoxy-4-[1 S-(1,4,6/5)-4,5,6-trihydroxy-3-hydroxymethylcyclohex-2-en-1-ylamino]-α-D-glucopyranosyl}-(1→4)-O-α-D-glucopyranosyl- (1→4)-D-glucopyranose of the conformational structural formula:

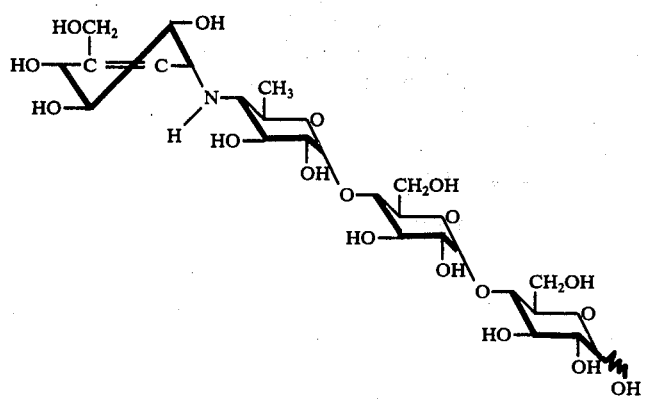

(1→4)-O-α-D-glucopyranosyl-(1→4)-D-glycopyranose of the conformational structural formula:

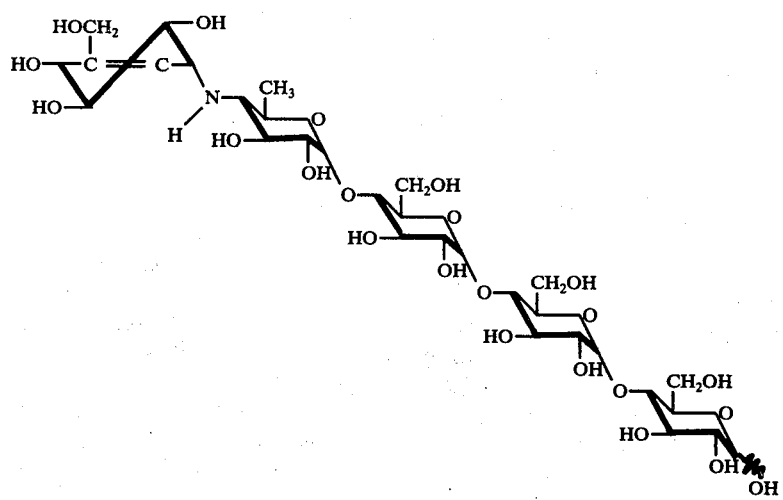

9. A composition according to claim 3 comprising at least one of said amino sugars wherein the sum of $x + y$ is 3.

10. A composition according to claim 9 wherein said amino sugar is O-{4,5-bisdesoxy-4-[1 S-(1,4,6/5)-4,5,6-trihydroxy-3-hydroxymethylcyclohex-2-en-1-ylamino]-α-D-glucopyranosyl}-(1→4)-O-α-D-glucopyranosyl- 11. A composition according to claim 9 wherein said amino sugar is O-{4,6-bisdesoxy-4-[1 S-(1,4,6/5)-5,6-dihydroxy-3-hydroxymethyl-4-O-α-D-glycopyranosyl-(1→4)-cyclohex-2-en-1-ylamino]-α-D-glycopyranosyl}-(1→4)-O-α-D-glycopyranosyl-(1→4)-D-glucopyranose of the conformational structural formula:

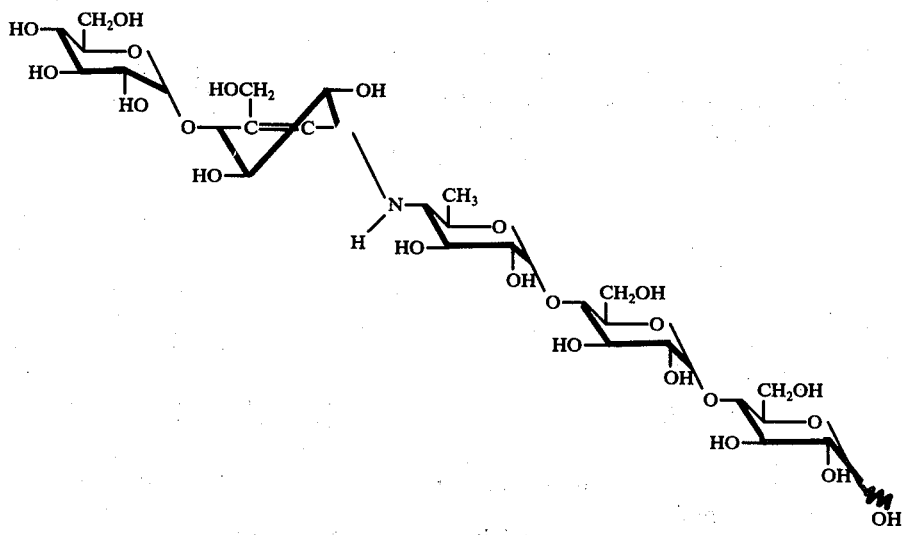

12. A composition according to claim 3 comprising at least one of said amino sugars wherein the sum of $x + y$ is 4.

13. A composition according to claim 12 wherein said amino sugar has the formula:

14. A composition according to claim 3 comprising at least one of said amino sugars wherein the sum of $x + y$ is 5.

15. A composition according to claim 14 wherein said amino sugar has the formula:

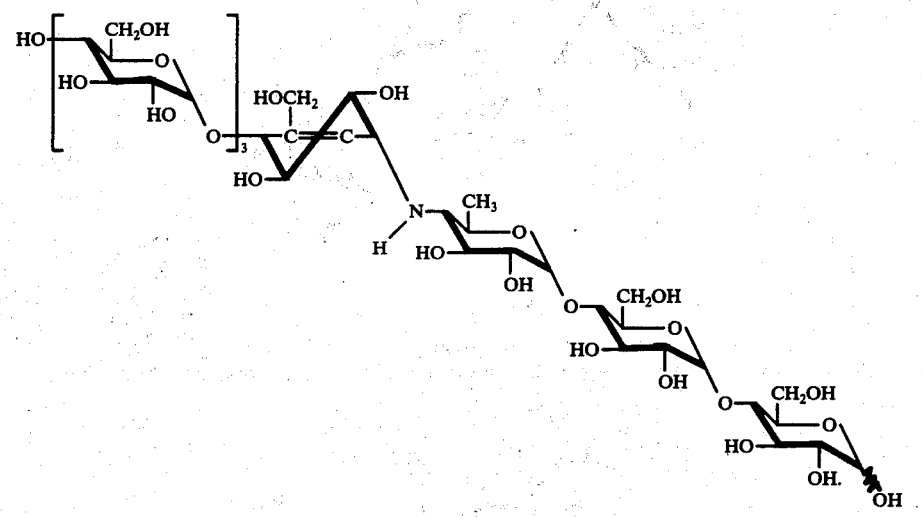

16. A composition according to claim 3 comprising at least one of said amino sugars wherein the sum of $x + y$ is 6.

17. A composition according to claim 16 wherein said amino sugar has the formula:

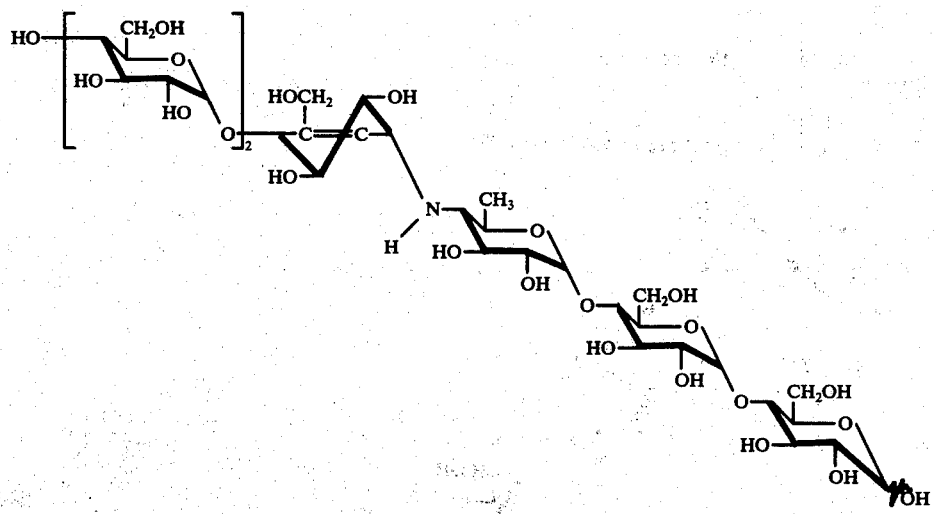

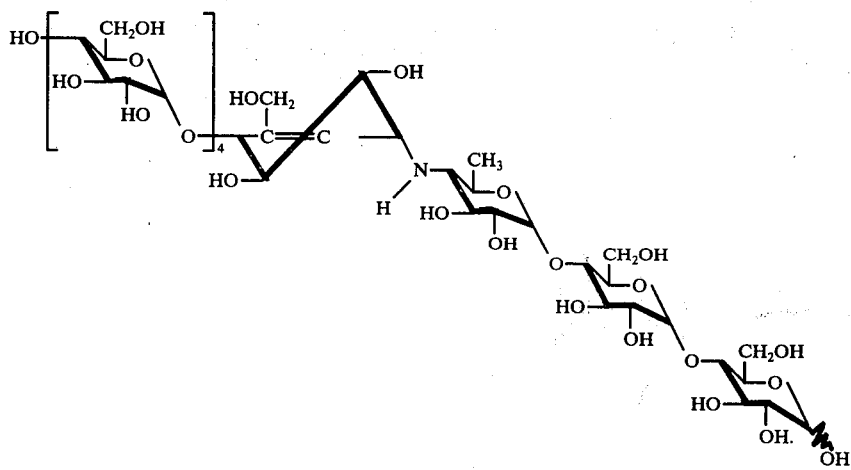

18. A composition according to claim 3 comprising at least one of said amino sugars wherein the sum of $x + y$ is 7.

19. A composition according to claim 18 wherein said amino sugar has the formula:

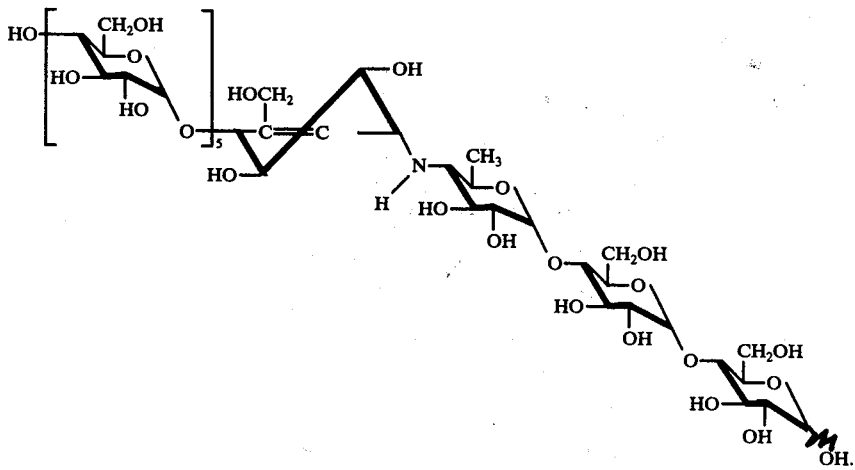

20. A composition according to claim 3 comprising at least one of said amino sugars wherein the sum of $x + y$ is 8.

21. A composition according to claim 20 wherein said amino sugar has the formula:

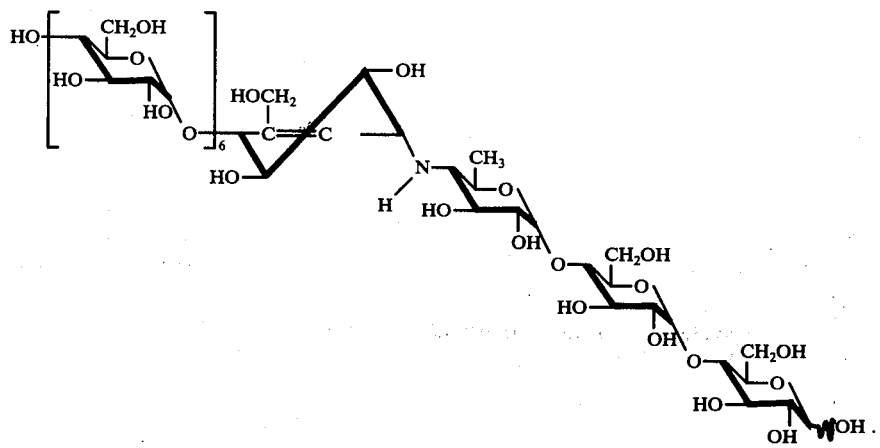

22. A composition according to claim 2 wherein said carrier is water.

23. A composition according to claim 2 wherein said carrier is animal feedstuff.

24. The method of influencing the utilization of feed in an animal by reducing formation of fat and thereby increasing the meat:fat ratio in the animal in favor of a higher proportion of meat which comprises orally administering to said animal an effective amount of at least one amino-sugar as herein defined, said amino-sugar chemically consisting of a 4,6-bidesoxy-4-(4,5,6-trihydroxy-3-hydroxymethylcyclohex-2-en-1-ylamino)-α-D-glucopyranose of the formula:

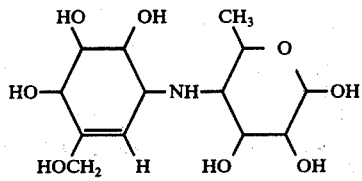

glycosidically linked with *n* glucose residues, where *n* is 1 to 40, which, when present in a polymeric chain of two or more glucose residues, are linked α-1:4, said amino-sugar yielding upon total acid hydrolysis the compound

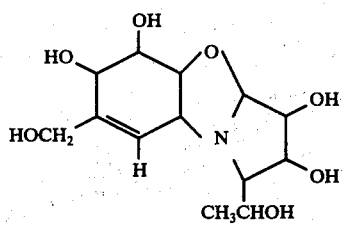

and glucose in a molar ratio of 1:*n* where *n* is as defined above.

25. The method of influencing the utilization of feed in an animal by reducing formation of fat and thereby increasing the meat:fat ratio in the animal in favor of a higher proportion of meat which comprises orally administering to said animal an effective amount of at least one amino-sugar as herein defined, said amino-sugar having the conformational formula:

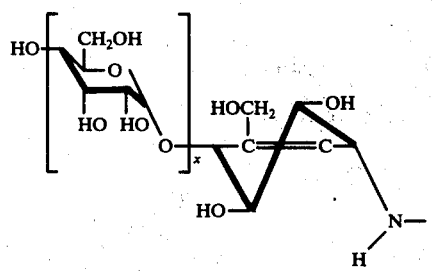

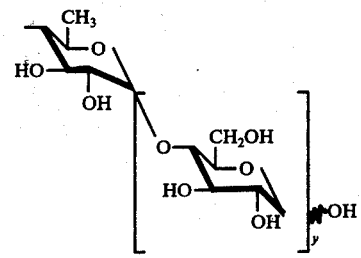

wherein
  *y* has a value of 1 to 8 and
  *x* has a value of from 0 to 7,
  the sum of *y* + *x* being from 1 to 8.

26. The method according to claim 25 in which there is administered a mixture of said amino-sugars for which mixture the average value for the sum of $x + y$ is from 1 to about 4.

27. The method according to claim 25 in which there is administered a single substantially pure amino-sugar for which the sum of $x + y$ is 1, 2, 3 or 4.

28. The method according to claim 25 in which there is administered at least one amino-sugar wherein the sum of $x + y$ is 1.

29. The method according to claim 28 wherein said amino-sugar is O-{4,6-bisdesoxy-4-[1 S-(1,4,6/5)4,5,6-trihydroxy-3-hydroxymethylcyclohex-2-en-1-ylamino]-α-D-glucopyranosyl}-(1→4)-D-glucopyranose of the conformational structural formula:

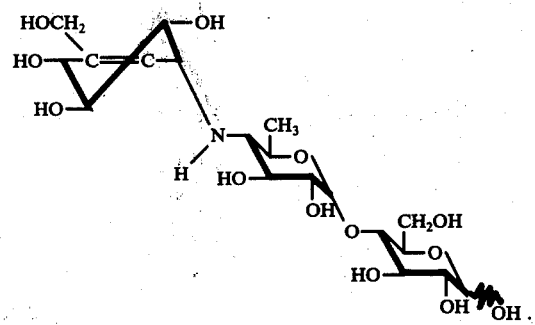

30. The method according to claim 25 in which there is administered at least one amino-sugar wherein the sum of $x + y$ is 2.

31. The method according to claim 30 wherein said amino-sugar is O-{4,6-bisdesoxy-4-[1 S-(1,4,6/5)-4,5,6-trihydroxy-3-hydroxymethylcyclohex-2-en-1-ylamino}-α-D-glucopyranosyl}-(1→4)-O-α-D-glucopyranosyl-(1→4)-D-glucopyranose of the conformational structural formula:

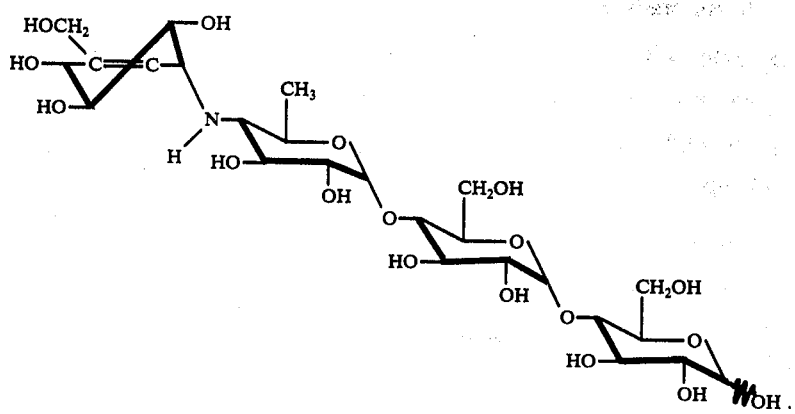

32. The method according to claim 25 in which there is administered at least one amino-sugar wherein the sum of $x + y$ is 3.

33. The method according to claim 32 wherein said amino-sugar is O-{4,5-bisdexosy-4-[1 S-(1,4,6/5)-4,5,6-trihydroxy-3-hydroxymethylcyclohex-2-en-1-ylamino}-α-D-glucopyranosyl}-(1→4)-O-α-D-glucopyranosyl-(1→4)-O-α-D-glucopyranosyl-(1→4)- D-glycopyranose of the conformational structural formula:

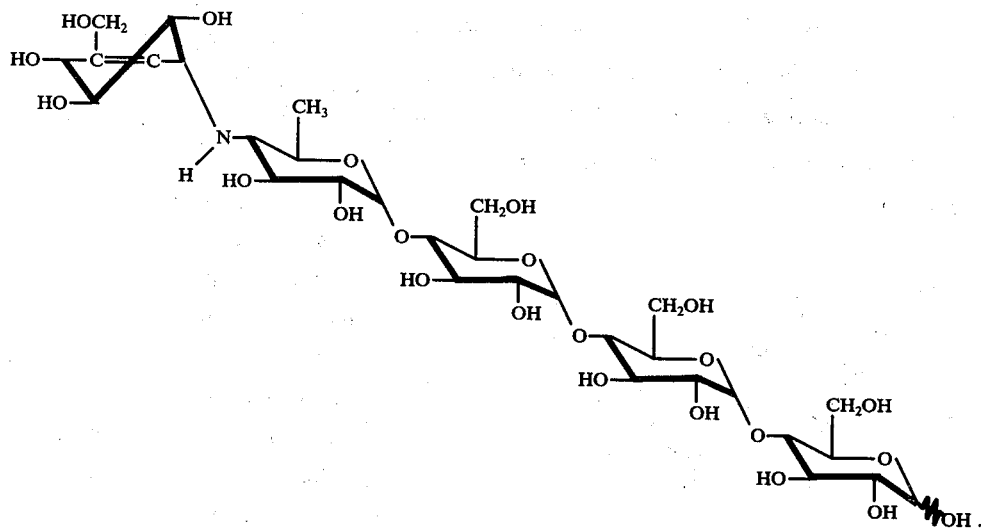

34. The method according to claim 32 wherein said amino-sugar is O-{4,6-bisdesoxy-4-[1 S-(1,4,6/5)-5,6-dihydroxy-3-hydroxymethyl-4-O-α-D-glycopyranosyl-(1→4)-cyclohex-2-en-1-ylaminoπ-α-D-glycopyranosyl]-(1→4)-O-α-D-glucopyranosyl-(1→4)-D-glucopyranose of the conformational structural formula:

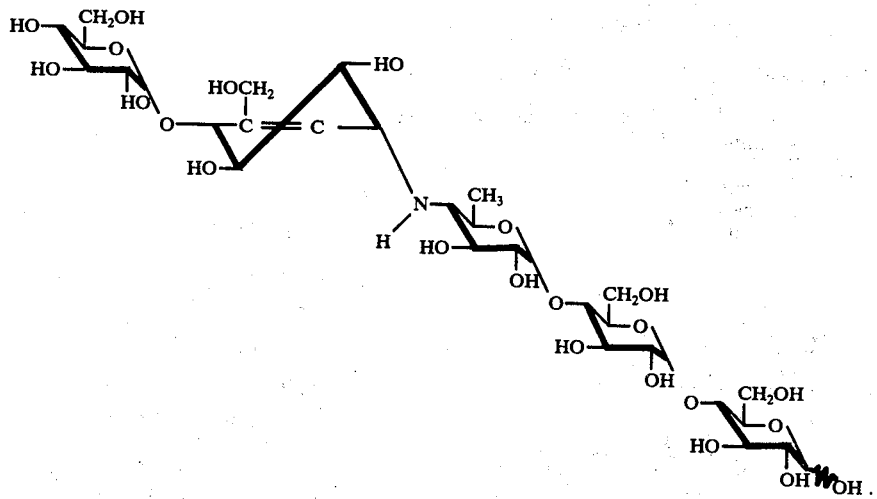

35. The method according to claim 25 in which there is administered at least one amino sugar wherein the sum of $x + y$ is 4.

36. The method according to claim 35 wherein said amino-sugar has the formula:

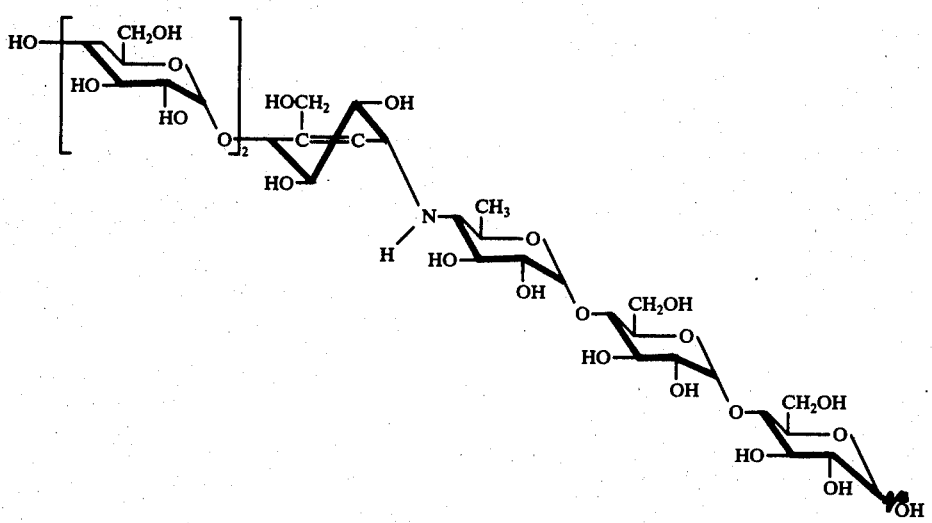

37. The method according to claim 25 wherein said amino-sugar is administered to said animal in drinking water.

38. The method according to claim 25 wherein said amino sugar is administered to said animal in admixture with animal feedstuff.

* * * * *